US008951983B2

(12) United States Patent
Hornstein et al.

(10) Patent No.: US 8,951,983 B2
(45) Date of Patent: Feb. 10, 2015

(54) METHODS AND COMPOSITIONS FOR THE TREATMENT OF INSULIN-ASSOCIATED MEDICAL CONDITIONS

(75) Inventors: Eran Hornstein, Rehovot (IL); Tal Melkman-Zehavi, Rehovot (IL); Roni Oren, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/879,843

(22) PCT Filed: Oct. 10, 2011

(86) PCT No.: PCT/IB2011/054446
§ 371 (c)(1),
(2), (4) Date: Apr. 17, 2013

(87) PCT Pub. No.: WO2012/052872
PCT Pub. Date: Apr. 26, 2012

(65) Prior Publication Data
US 2013/0209440 A1    Aug. 15, 2013

Related U.S. Application Data

(60) Provisional application No. 61/393,900, filed on Oct. 17, 2010.

(51) Int. Cl.
*A61K 48/00* (2006.01)
*C07H 21/02* (2006.01)
*C07H 21/04* (2006.01)

(52) U.S. Cl.
USPC .......................... 514/44; 536/23.1; 536/24.5

(58) Field of Classification Search
CPC .. C12N 2830/002; C12N 15/63; C12N 15/85; A61K 31/7088; A61K 48/0066
See application file for complete search history.

(56) References Cited

U.S. PATENT DOCUMENTS

| 2005/0227934 A1 | 10/2005 | Stoffel et al. |
| 2009/0131348 A1 | 5/2009 | Labourier et al. |
| 2009/0291907 A1 | 11/2009 | Esau et al. |

FOREIGN PATENT DOCUMENTS

| WO | WO 2007/081740 | 7/2007 |
| WO | WO 2009/067644 | 5/2009 |
| WO | WO 2012/052872 | 4/2012 |

OTHER PUBLICATIONS

Ozcan, Islets 1:3, 283-285, 2009.*
Communication Relating to the Results of the Partial International Search Dated Feb. 16, 2012 From the International Searching Authority Re. Application No. PCT/IB2011/054446.
International Search Report and the Written Opinion Dated Aug. 31, 2012 From the International Searching Authority Re. Application No. PCT/TB2011/054446.
Baroukh et al. "MicroRNA-124a Regulates Foxa2 Expression and Intracellular Signaling in Pancreatic B-Cell Lines", The Journal of Biological Chemistry, 282(27): 19575-19588, Jul. 6, 2007.
El Quaamari et al. "MiR-375 Targets 3'-Phosphoinositide-Dependent Protein Kinase-1 and Regulates Glucose-Induced Biological Responses in Pancreatic β-Cells", Diabetes, 57: 2708-2717, Oct. 2008.
Mclkman-Zehavi et al. "MiRNAs Control Insulin Content in Pacreatic Beta-Cells Via Downregulation of Transcriptional Repressors", The EMBO Journal, XP055017780, 30(5): 835-845, Mar. 2011.
Pandey et al. "MicroRNAs in Diabetes: Tiny Players in Big Disease", Cellular Physiology and Biochemistry, XP009156027, 23(4-6): 221-232, 2009. Abstract, p. 222, col. 2, Para 3—p. 225, col. 1, Para 1.
Poy et al. "A Pancreatic Islet-Specific MicroRNA Regulates Insulin Secretion", Nature, 432: 226-230, Nov. 11, 2004.
Poy et al. "MiR-375 Maintains Normal Pancreatic α- and β-Cell Mass", Proc. Natl. Acad. Sci. USA, PNAS, 106(14): 5813-5818, Apr. 7, 2009.
Roggli et al. "Involvement of MicroRNAs in the Cytotoxic Effects Exerted by Proinflammatory Cytokines on Pancreatic β-Cells", Diabetes, 59: 978-986, Apr. 2010.
Tang et al. "Identification of Glucose-Regulated MiRNAs From Pancreatic Beta Cells Reveals a Role for MiR-30d in Insulin Transcription", RNA, XP002598119, 15(2): 287-293, Feb. 1, 2009.
Tattikota et al. "Re-Dicing the Pancreatic Beta-Cell: Do MicroRNAs Define Cellular Identity?" The EMBO Journal, XP009162202, 30(5): 797-799, Mar. 2011.
Xia et al. "Over-Expression of MiR375 Reduces Glucose-Induced Insulin Secretion in Nit-1 Cells", Molecular Biology Reports, 5 P., Published Online on Feb. 3, 2010.
International Preliminary Report on Patentability Dated May 2, 2013 From the International Bureau of WIPO Re. Application No. PCT/IB2011/054446.
Communication Pursuant to Article 94(3) EPC Dated Feb. 12, 2014 From the European Patent Office Re. Application No. 11779487.5.
Communication Pursuant to Article 94(3) EPC Dated Nov. 24, 2014 From the European Patent Office Re. Application No. 11779487.5.

* cited by examiner

*Primary Examiner* — Amy Bowman

(57) ABSTRACT

A method of increasing insulin content in a pancreatic beta cell is disclosed. The method comprising expressing in the pancreatic beta cell an exogenous polynucleotide encoding at least one microRNA or a precursor thereof, wherein the microRNA is selected from the group consisting of miR-15, miR-16, miR-24, miR-26, miR-27, miR-29, miR-30, miR-129, miR-141, miR-148, miR-182, miR-200, miR-376 and Let-7, thereby increasing the insulin content in the pancreatic beta cell.

5 Claims, 17 Drawing Sheets
(7 of 17 Drawing Sheet(s) Filed in Color)

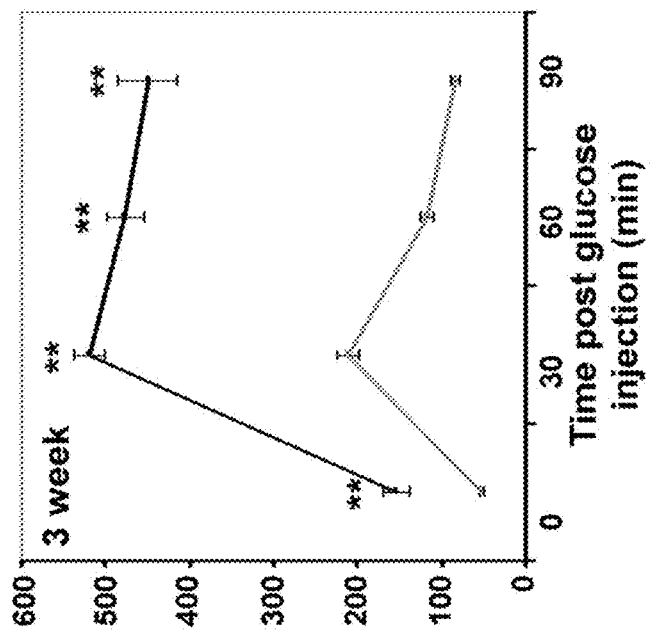
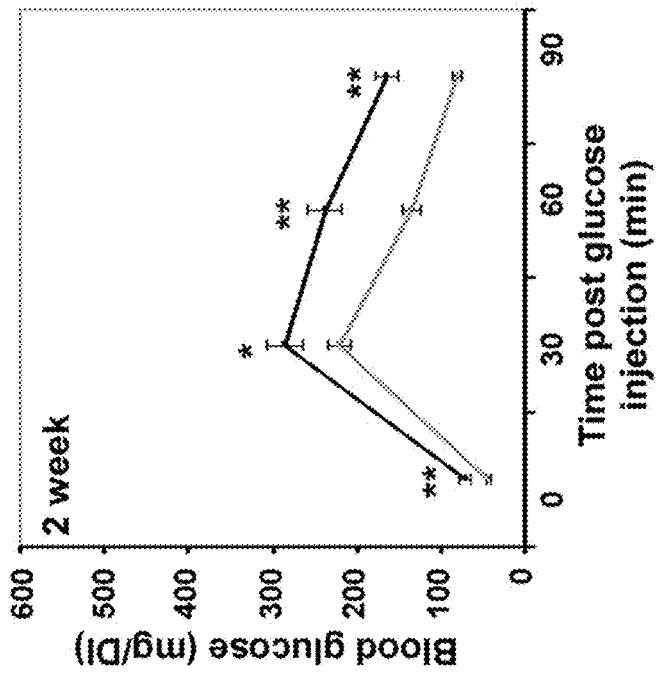
FIG. 2C
FIG. 2D

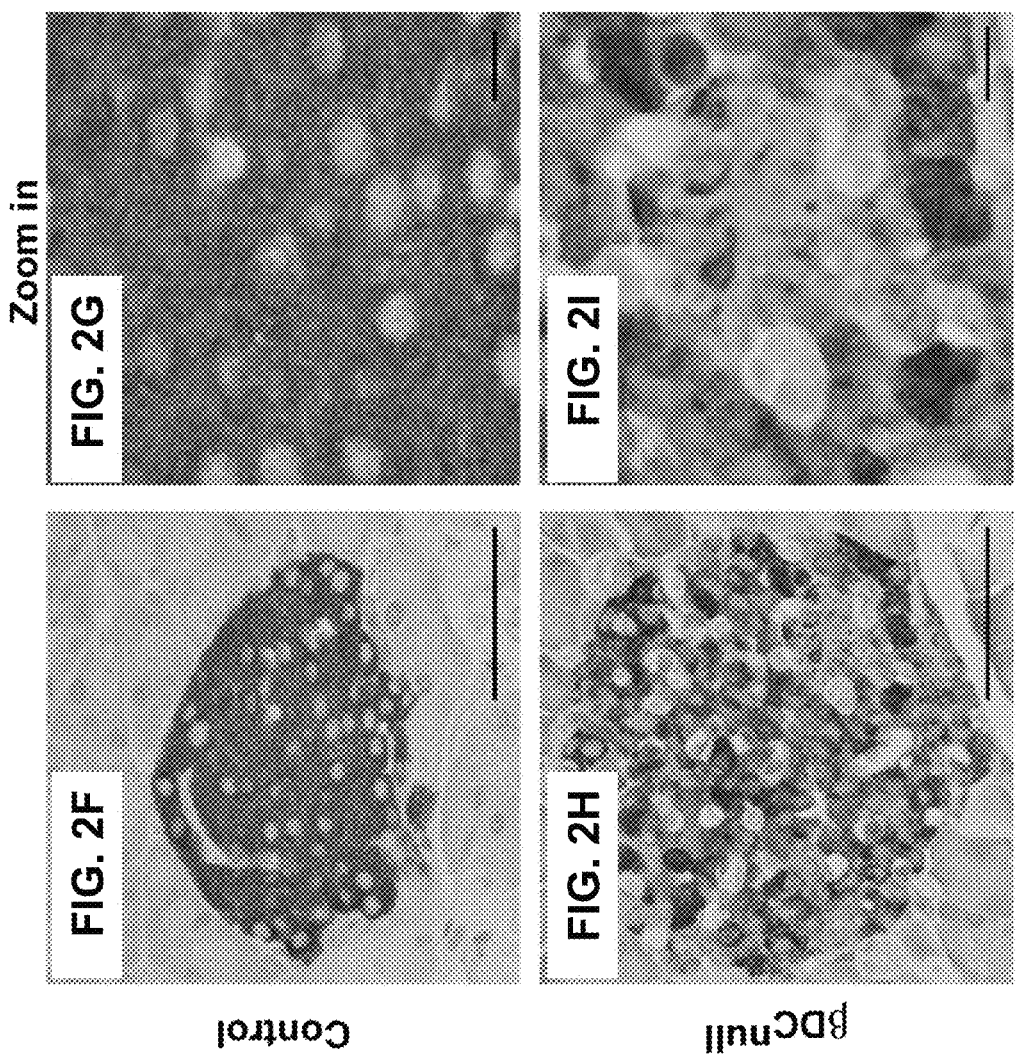

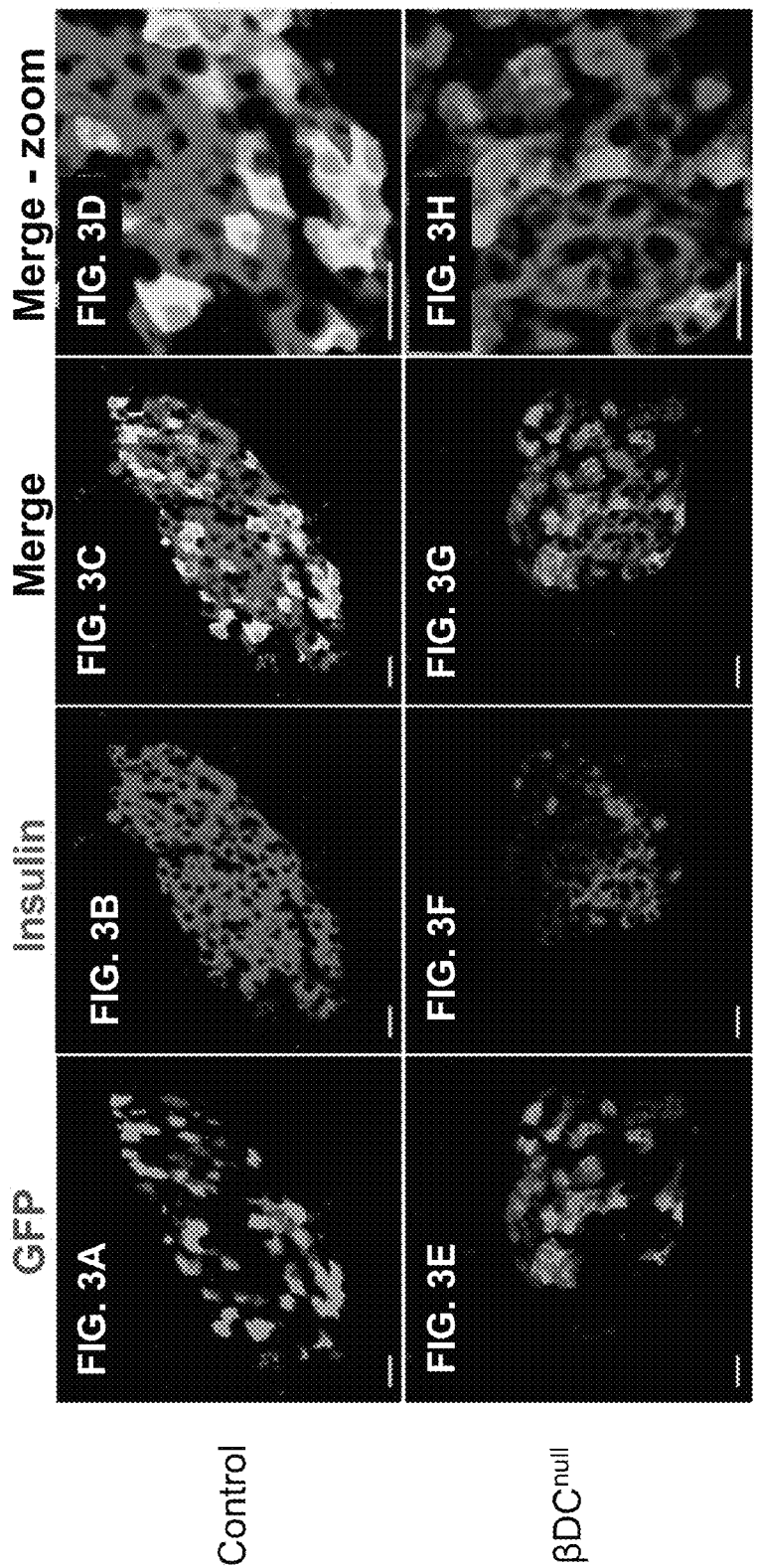

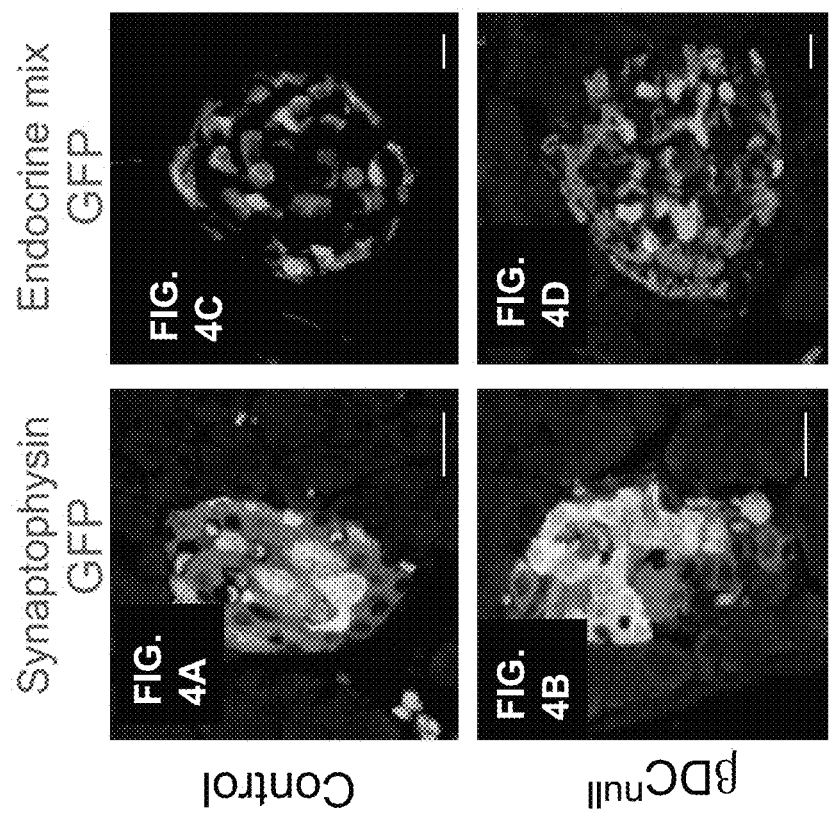

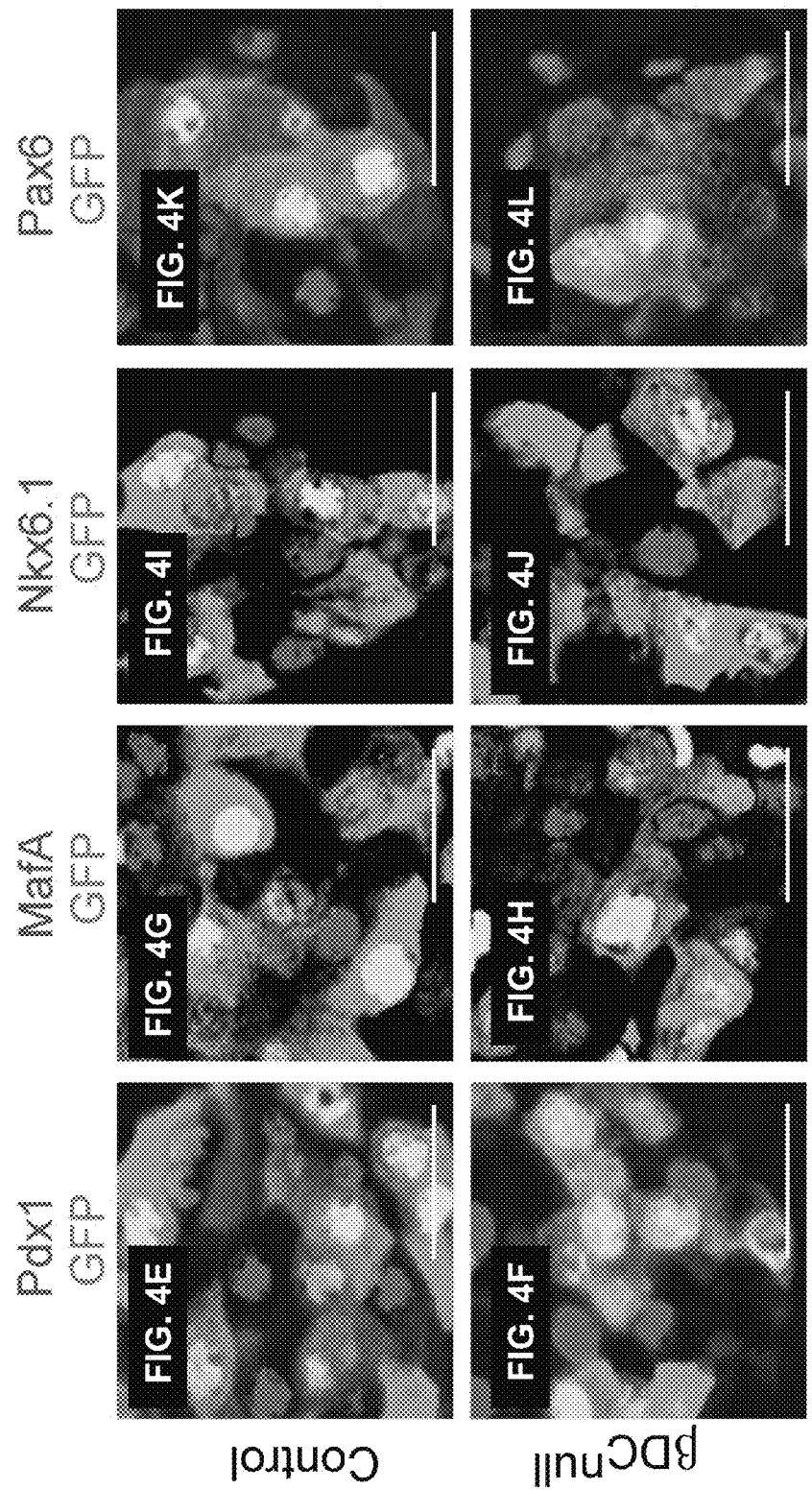

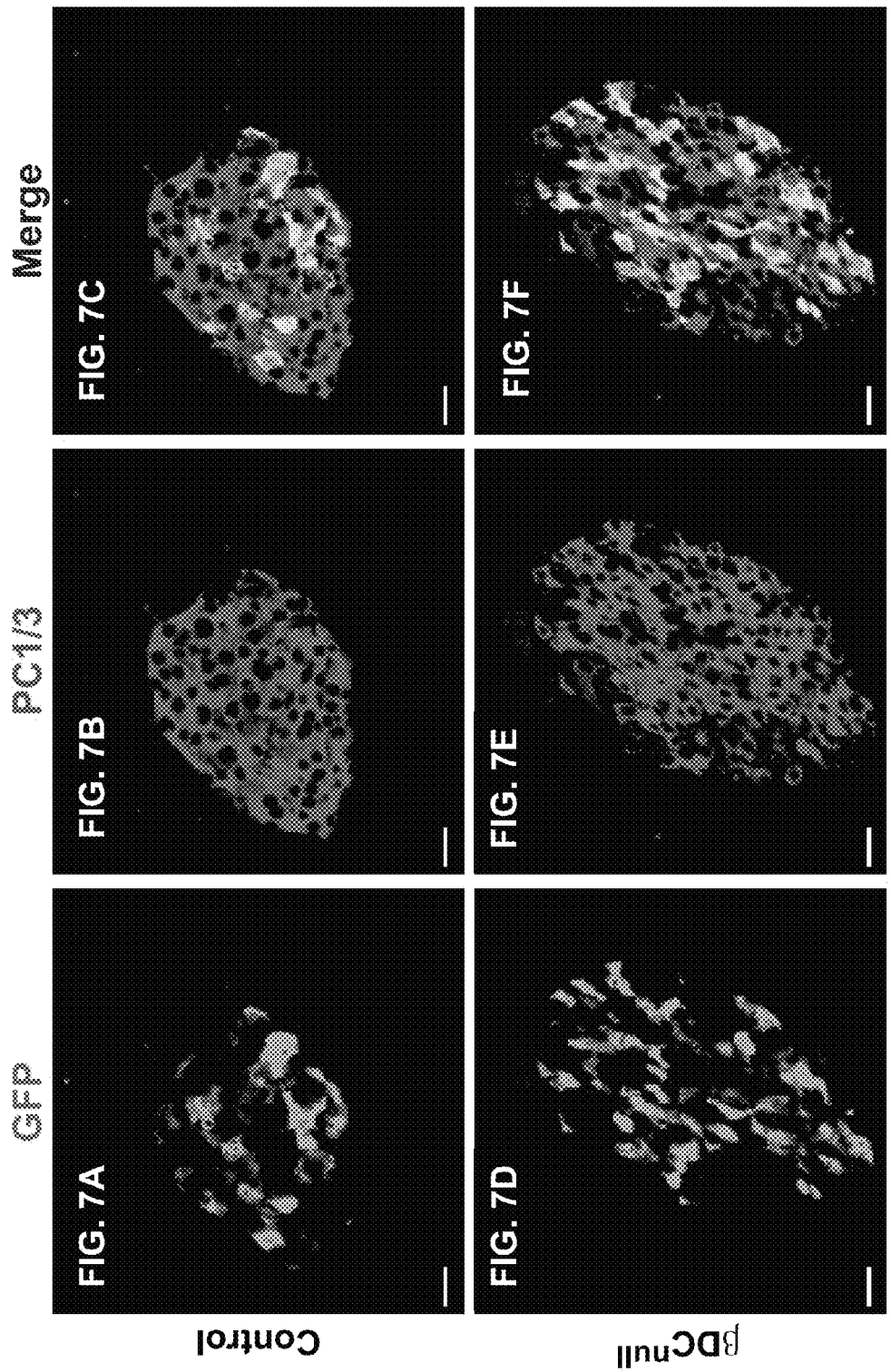

METHODS AND COMPOSITIONS FOR THE TREATMENT OF INSULIN-ASSOCIATED MEDICAL CONDITIONS

RELATED APPLICATIONS

This application is a National Phase of PCT Patent Application No. PCT/IB2011/054446 having International filing date of Oct. 10, 2011, which claims the benefit of priority under 35 USC §119(e) of U.S. Provisional Patent Application No. 61/393,900 filed on Oct. 17, 2010. The contents of the above applications are all incorporated by reference as if fully set forth herein in their entirety.

SEQUENCE LISTING STATEMENT

The ASCII file, entitled 55689SequenceListing.txt, created on Jan. 15, 2013, comprising 1,573,025 bytes, submitted concurrently with the filing of this application is incorporated herein by reference.

FIELD AND BACKGROUND OF THE INVENTION

The present invention, in some embodiments thereof, relates to microRNAs, more particularly, but not exclusively, to expression or repression of same in pancreatic beta cells for modulation of insulin levels.

In adult beta cells, insulin transcription is tightly regulated by a network of transcriptional activators and repressors. A few transcriptional repressors of the Insulin gene have been characterized, including, NRx2.2, Insm1 (Insulinoma-Associated 1/IA1), Sox6, Bhlhe22 and Crem. Transcription activators have also been characterized including Pdx1, MafA, NeuroD, Pax6 and Isl1 which maintain the beta cell fate and activate insulin transcription in response to elevation in plasma glucose. Thus, a fine balance between these opposing transcription factors must be kept for effective insulin synthesis.

The recently discovered microRNA (miRNA) family of posttranscriptional regulators, provide an additional regulatory layer that may play an important role in the adult endocrine pancreas. miRNAs are important for beta cell differentiation and specific miRNAs have been proposed to regulate beta cell genes. For example, miR-124a was shown to affect the expression of FoxA2 and Pdx1, the secretory pathway proteins, SNAP25 and Rab3a, as well as the ion channels Kir6.2 and Sur1 [Baroukh, N. et al. (2007) J Biol Chem 282, 19575-19588; El Ouaamari A. et al. (2008) Diabetes 57, 2708-2717].

The involvement of miRNAs in insulin secretion has also been contemplated. Poy et al. have shown that miR-375 affects insulin secretion through regulation of myotrophin expression, specifically, they showed that over-expression of miR-375 suppressed glucose-induced insulin secretion, and conversely, inhibition of endogenous miR-375 function enhanced insulin secretion [Poy M. N. et al. (2004) Nature 432, 226-230]. Xia et al. have shown that over-expression of miR375 reduces glucose-induced insulin secretion by down-regulating the expression of myotrophin in Nit-1 cells [Xia et al., Mol Biol Rep. (2010) Epub ahead of print]. Roggli E. et al. have shown an increase in miR-21, miR-34a and miR-146a in islets of NOD mice during development of pre-diabetic insulitis. According to their teachings, overexpression of miR-21 or miR-146a did not significantly affect insulin content, insulin promoter activity or pro-insulin mRNA levels, while over-expression of miR-34a led to a decrease in insulin content and insulin promoter activity accompanied by a reduction in pro-insulin mRNA level [Roggli E. et al., Diabetes (2010) 59(4): 978-86].

To date, the only knockout model for an islet-enriched miRNA is the mouse knockout for miR-375. Genetic loss of miR-375 causes decreased beta cell mass due to impaired proliferation. Additionally, miR-375 mutants have increased alpha cell numbers, increased plasma level of glucagon and increased gluconeogenesis in the liver [Poy M. N. et al. (2009) Proc Natl Acad Sci USA]. Thus miR-375 provides an intriguing endocrine phenotype that encourages further evaluation of the role of miRNAs in vivo.

miRNAs are subject to extensive processing, including digestion by Drosha in the nucleus and by Dicer1 in the cytoplasm. Deletion of Dicer1 in the early pancreatic lineage, using a Pdx1-Cre mouse line resulted in inactivation of the entire miRNA pathway in the early pancreatic bud. This early inactivation of Dicer 1 causes pancreas agenesis, suggesting that miRNA are indeed important for pancreas organogenesis.

U.S. Application No. US 2009/0131348 describes methods and compositions of identifying a miRNA expression profile for a medical condition, such as pancreatic disease, and subsequently disclose methods for diagnosing and treating such as condition, by for example, downregulation of miRNA or by administration of synthetic miRNA molecules.

U.S. Application No. US 2005/227934 describes pancreatic islet microRNAs and methods for inhibiting same. Specifically, U.S. Application No. US 2005/227934 teaches anti-pancreatic islet microRNA molecules which are capable of inhibiting pancreatic islet microRNAs and use of same for treating diabetes.

SUMMARY OF THE INVENTION

According to an aspect of some embodiments of the present invention there is provided a method of increasing an insulin content in a pancreatic beta cell, the method comprising expressing in the pancreatic beta cell an exogenous polynucleotide encoding at least one microRNA or a precursor thereof, wherein the microRNA is selected from the group consisting of miR-15, miR-16, miR-24, miR-26, miR-27, miR-29, miR-30, miR-129, miR-141, miR-148, miR-182, miR-200, miR-376 and Let-7, thereby increasing the insulin content in the pancreatic beta cell.

According to an aspect of some embodiments of the present invention there is provided a method of treating a condition associated with an insulin deficiency in a subject in need thereof, the method comprising administering to the subject an exogenous polynucleotide encoding at least one microRNA or a precursor thereof, wherein the microRNA is selected from the group consisting of miR-15, miR-16, miR-24, miR-26, miR-27, miR-29, miR-30, miR-129, miR-141, miR-148, miR-182, miR-200, miR-376 and Let-7, thereby treating the condition associated with an insulin deficiency.

According to an aspect of some embodiments of the present invention there is provided a polynucleotide encoding at least one microRNA or a precursor thereof, wherein the microRNA is selected from the group consisting of miR-15, miR-16, miR-24, miR-26, miR-27, miR-29, miR-30, miR-129, miR-141, miR-148, miR-182, miR-200, miR-376 and Let-7 for treating a condition associated with an insulin deficiency.

According to an aspect of some embodiments of the present invention there is provided a nucleic acid construct comprising a nucleic acid sequence encoding a microRNA or a precursor thereof the nucleic acid sequence being operably linked to a pancreatic beta cell specific promoter.

According to an aspect of some embodiments of the present invention there is provided a pharmaceutical composition comprising the nucleic acid construct of claim 6 or 7 and a pharmaceutically acceptable carrier.

According to an aspect of some embodiments of the present invention there is provided an isolated pancreatic beta cell comprising the nucleic acid construct of claim 6 or 7.

According to an aspect of some embodiments of the present invention there is provided a method of decreasing an insulin content in a pancreatic beta cell of a subject in need thereof, the method comprising administering to the subject an agent capable of downregulating expression of at least one microRNA, wherein the microRNA is selected from the group consisting of miR-15, miR-16, miR-24, miR-26, miR-27, miR-29, miR-30, miR-129, miR-141, miR-148, miR-182, miR-200, miR-376 and Let-7, thereby decreasing the insulin content in the pancreatic beta cell.

According to an aspect of some embodiments of the present invention there is provided a method of treating a condition associated with elevated insulin levels in a subject in need thereof, the method comprising administering to the subject an agent capable of downregulating expression of at least one microRNA in a pancreatic beta cell of the subject, wherein the microRNA is selected from the group consisting of miR-15, miR-16, miR-24, miR-26, miR-27, miR-29, miR-30, miR-129, miR-141, miR-148, miR-182, miR-200, miR-376 and Let-7, thereby treating the condition associated with elevated insulin levels.

According to some embodiments of the invention, the polynucleotide is operably linked to a cis acting regulatory element active in pancreatic beta cell.

According to some embodiments of the invention, the condition associated with an insulin deficiency comprises diabetes mellitus.

According to some embodiments of the invention, the microRNA is selected from the group consisting of miR-15, miR-16, miR-24, miR-26, miR-27, miR-29, miR-30, miR-129, miR-141, miR-148, miR-182, miR-200, miR-376 and Let-7.

According to some embodiments of the invention, the isolated pancreatic beta cell of claim 9 for the treatment of diabetes.

According to some embodiments of the invention, the agent capable of downregulating expression of at least one microRNA comprises an enzyme.

According to some embodiments of the invention, the enzyme comprises Dicer1.

According to some embodiments of the invention, the enzyme is selected from the group consisting of Drosha, Dicer1, TUT4, DGCR8, exportin 5, Argonaute1, Argonaute2, Argonaute3, Argonaute4, TRBP, smad4 and Ran.

According to some embodiments of the invention, the subject is a human subject.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
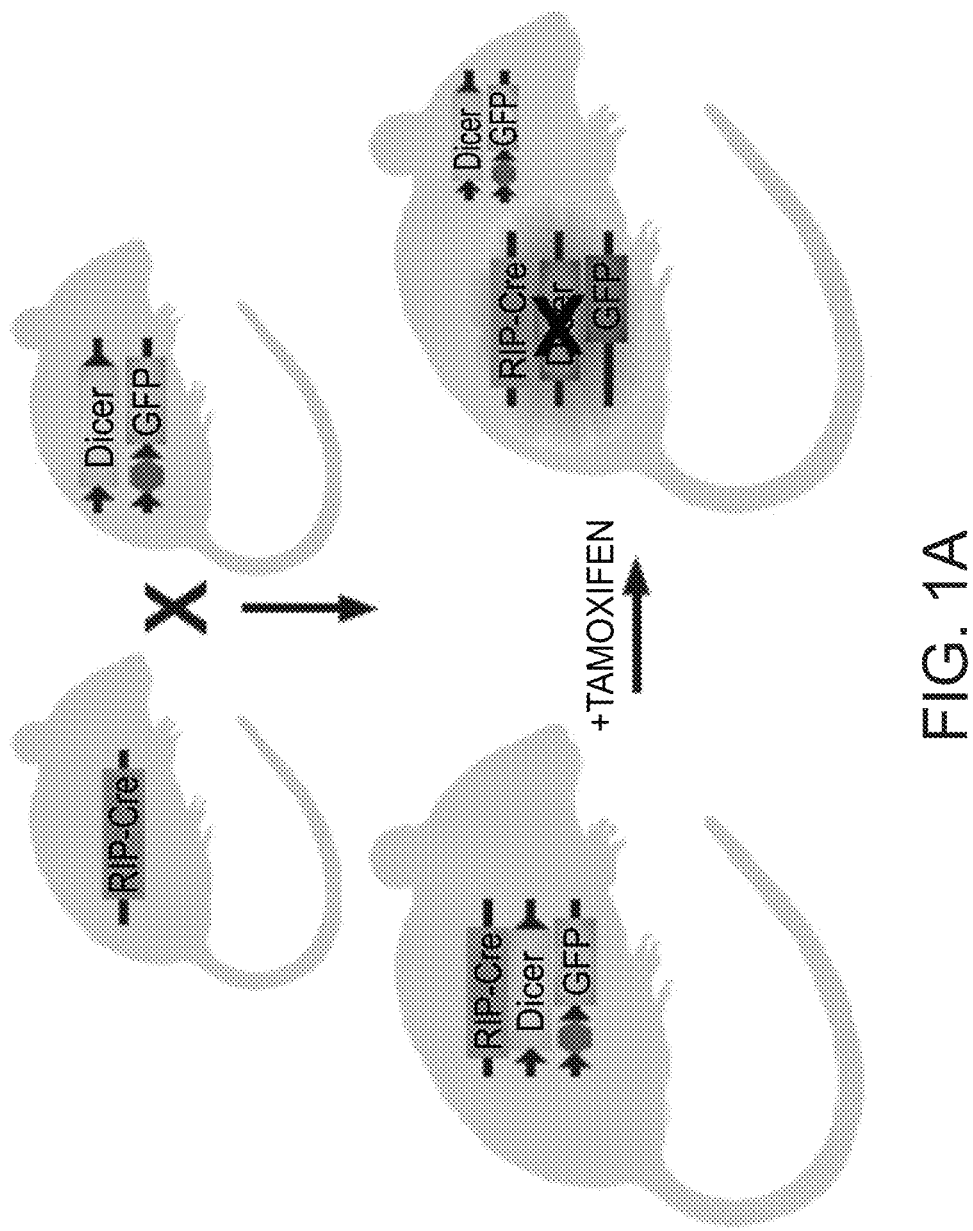
Figure 1C:
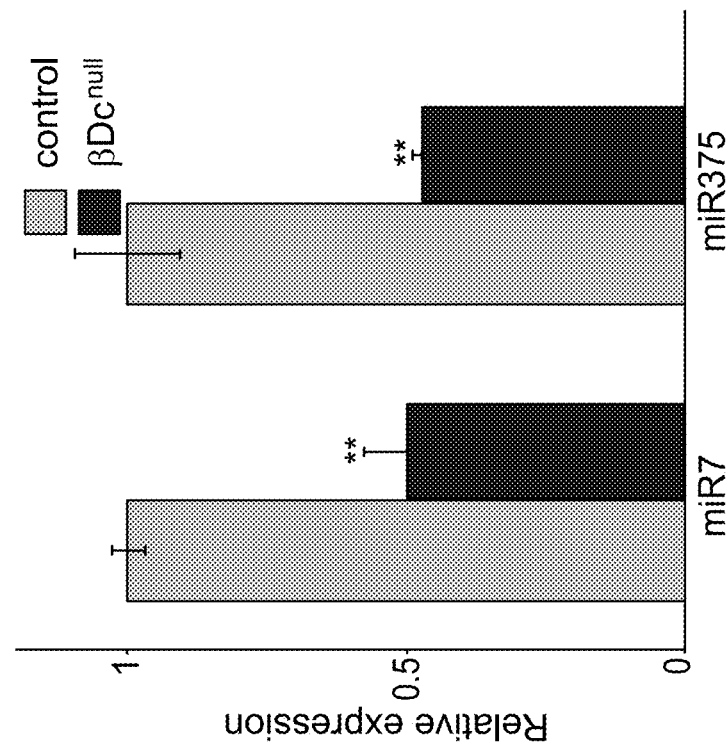
Figure 1B:
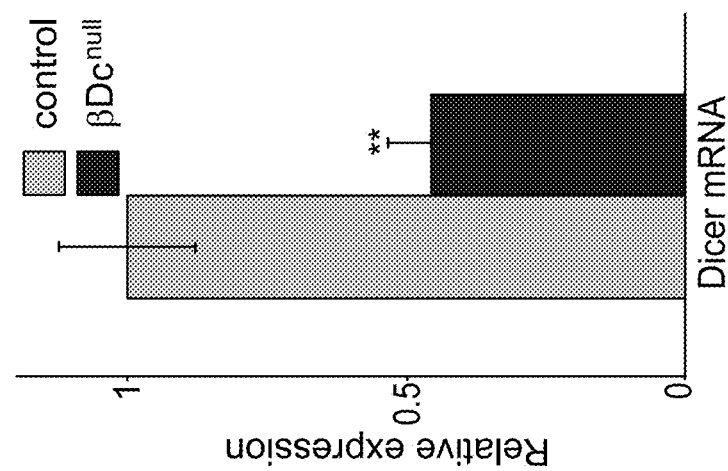

FIGS. 1A-C depict tamoxifen treatment-induced deletion of Dicer1 in mutant mice causes a reduction in Dicer1 and in miRNA levels. FIG. 1A shows Dicer disruption provoked by deletion of a floxed Dicer allele with the use of a tamoxifen-inducible Cre recombinase protein under the control of the pancreas specific rat insulin promoter (described in detail in the materials and experimental procedures section hereinbelow). Concomitant with Dicer deletion, Cre-mediated recombination activated EGFP expression by removal of a stop cassette that prevented its expression. qRT-PCR preformed on whole islets from control and $\beta Dc^{null}$ mice at 3 weeks post-induction showed a reduction in Dicer1 mRNA (FIG. 1B) and in two islet enriched miRNAs miR-7 and miR-375 (FIG. 1C).

Figure 2A:
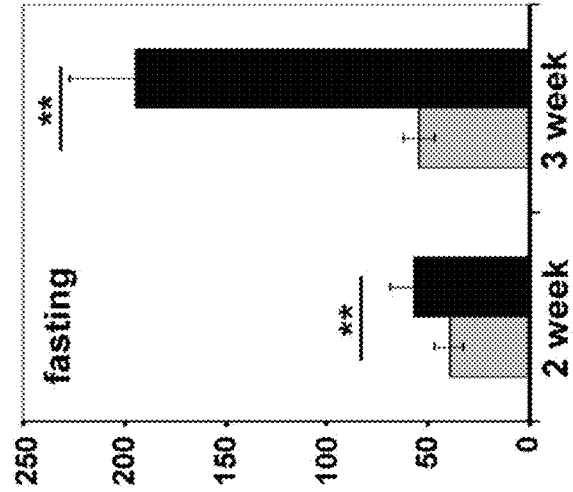
Figure 2B:
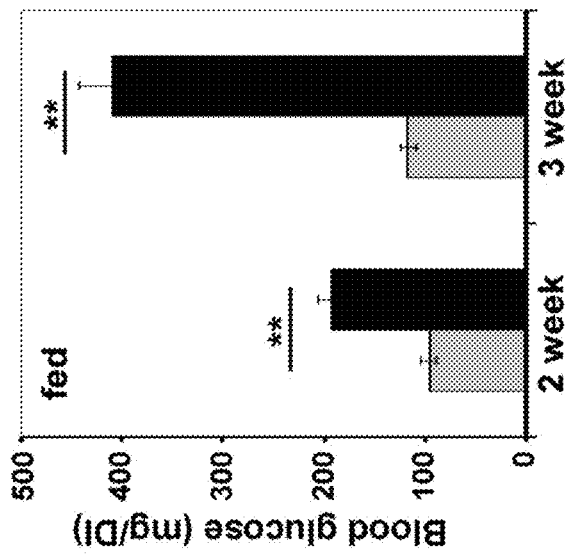
Figure 2E:
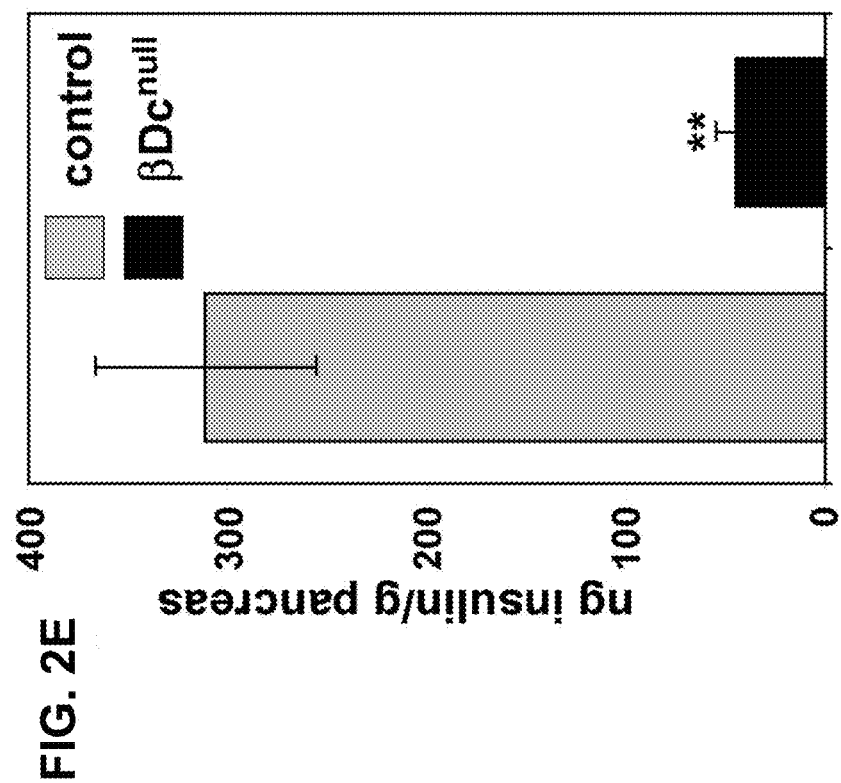

FIGS. 2A-I depict hyperglycemia and impaired glucose tolerance in $\beta Dc^{null}$ mice due to decreased insulin levels. FIGS. 2A-B show fed (FIG. 2A) and fasting (FIG. 2B) plasma glucose levels in control and $\beta Dc^{null}$ mice 2 and 3 weeks after tamoxifen treatment; FIGS. 2C-D show a glucose tolerance test performed 2 weeks (FIG. 2C) and 3 weeks (FIG. 2D) after tamoxifen treatment; FIG. 2E shows pancreatic insulin content three weeks after tamoxifen treatment; and FIGS. 2F-I show micrographs of insulin immunohistochemical staining of pancreas sections from control (FIGS. 2F-G) and $\beta Dc^{null}$ mice (FIG. 2H-I) 3 weeks after tamoxifen treatment. Panels 2G and 2I are a magnified view of 2F and 2H. Scale bar represents 20 μm.

Figure 2J:
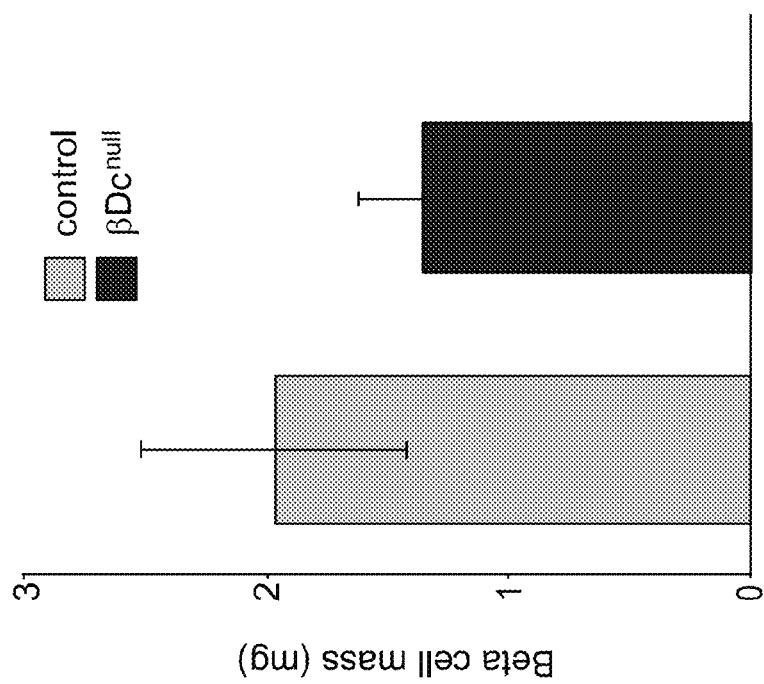

FIG. 2J depict similar beta cell mass of $\beta Dc^{null}$ animals compared to control mice. Analysis of pancreatic tissue that was isolated from age-matched animals at 3 weeks post Tamoxifen treatment. The mean (±SEM) islet cell mass of control (n=2) and $\beta Dc^{null}$ animals (n=3) tissues was calculated by morphometry.

Figures 3I, 3J, 3K:
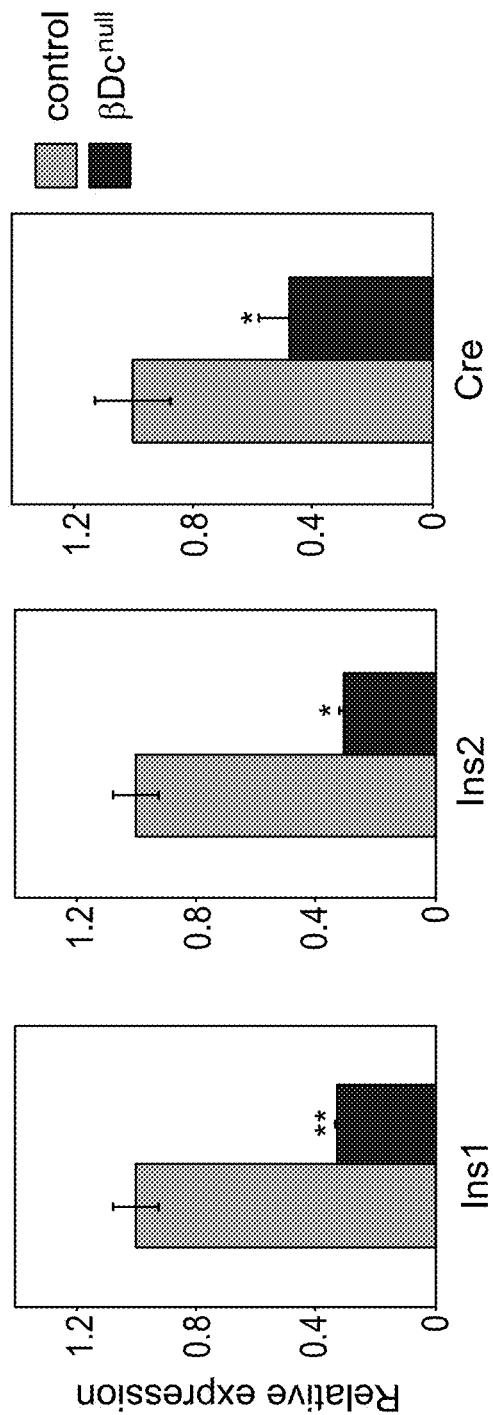

FIGS. 3A-K depict ceased insulin synthesis in $\beta Dc^{null}$ beta cells. Control (FIGS. 3A-3D) and $\beta Dc^{null}$ (FIGS. 3E-H) mice 3 weeks after tamoxifen treatment were stained for insulin (FIGS. 3B and 3F) and for GFP expression that marks the recombined cells within the islet (FIGS. 3A and 3E). The mosaic expression of GFP reflects incomplete induction by Tamoxifen. In the merged view (FIGS. 3C, 3D, 3G and 3H), co-localization of insulin and GFP staining yields a yellow color in control (FIGS. 3C and 3D) but not in $\beta Dc^{null}$ mice (FIGS. 3G and 3H). Scale bar represents 20 μm. FIGS. 3I-K show a reduction in the mRNA levels of insulin 1 (FIG. 3I), insulin 2 (FIG. 3J) and Cre (FIG. 3K) in $\beta Dc^{null}$ mice relative to control by qPCR analysis on isolated islets. Values shown are mean±SEM. * p<0.05, **p<0.01.

FIGS. 4A-L depict maintained beta cell characteristics and no acquired alternate endocrine markers in $\beta Dc^{null}$ beta cells. Immunofluorescent staining of the endocrine marker synaptophysin (marked by red, FIGS. 4A and 4B) and hormone markers—a mixture of antibodies raised against glucagon, Gehrlin, pancreatic polypeptide and somatostatin (marked by red, FIGS. 4C and 4D)—was indistinguishable between control (FIGS. 4A and 4C) and βDc$^{null}$ mutants (FIGS. 4B and 4D). Similarly, characteristic beta-cell transcription factors (marked by red) Pdx1 (FIGS. 4E and 4F) MafA (FIGS. 4G and 4H) NRx6.1 (FIGS. 4I and 4J) Pax6 (FIGS. 4K and 4L) were co-expressed with GFP (marked by green) both in controls (FIGS. 4E, 4G, 4I and 4K), and in βDc$^{null}$ mutants (FIGS. 4F, 4H, 4J and 4L). Scale bar represents 20 μm. Yellow indicates colocalization.

Figure 5A:
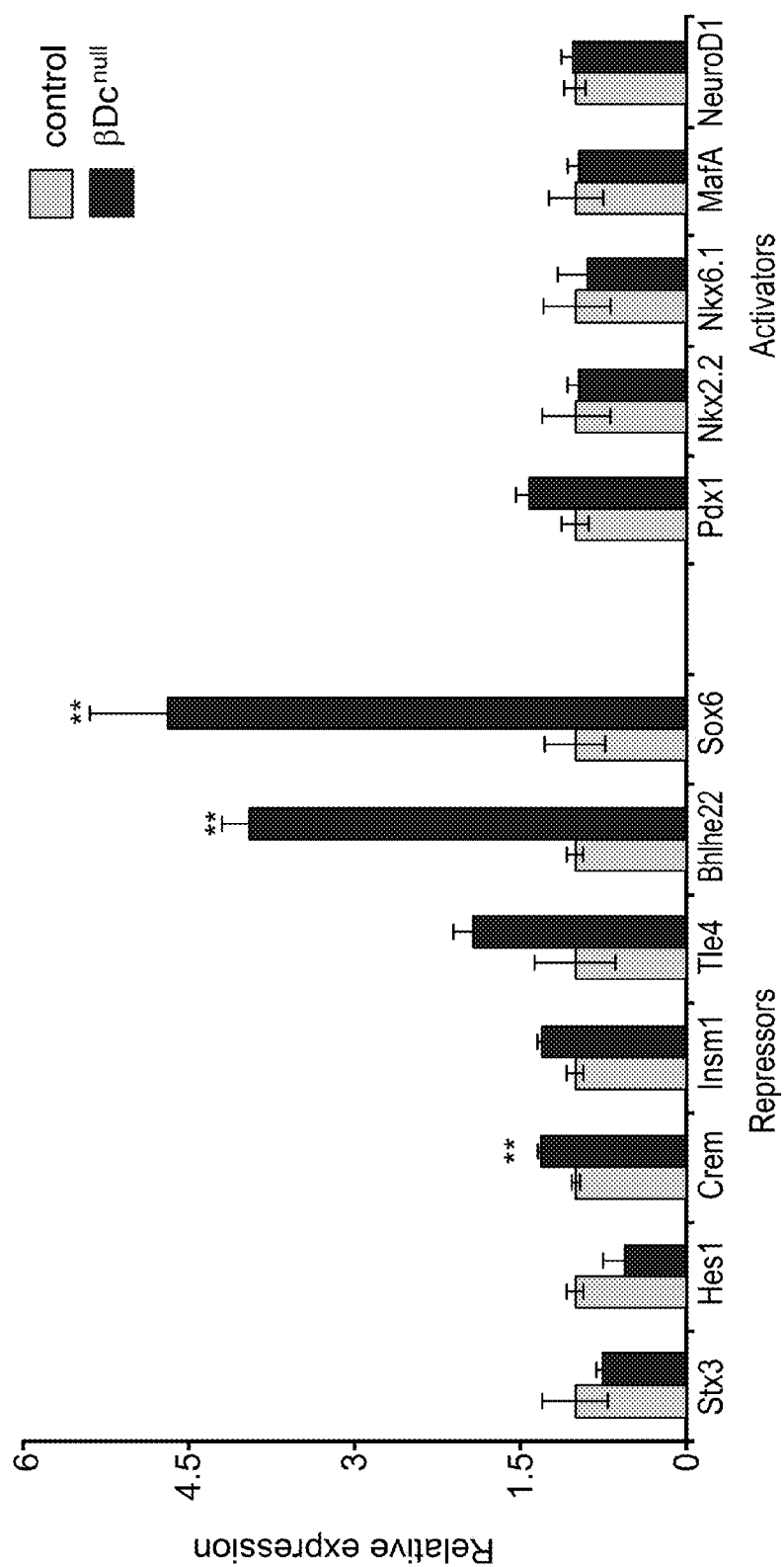
Figure 5B:
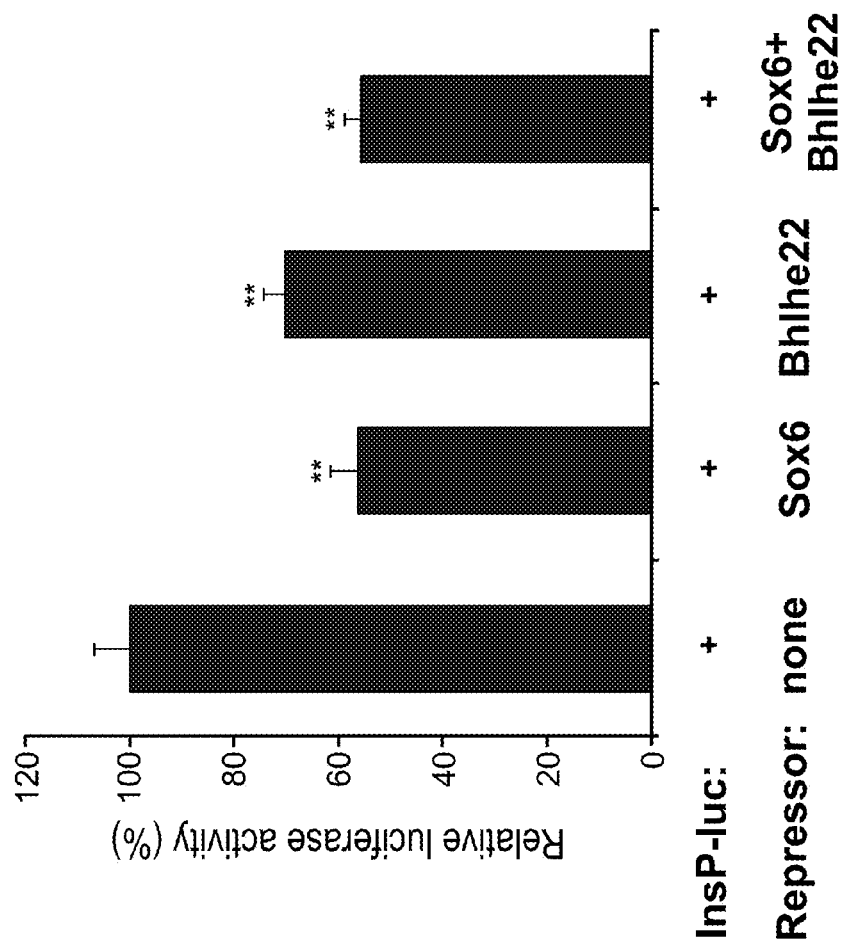

FIGS. 5A-B depict upregulated expression of transcriptional repressors of insulin in βDc$^{null}$ islets. qPCR study of RNA isolated from control and βDc$^{null}$ islets, revealed no significant change in the expression levels of the transcriptional activators Pdx1, Nkx2.2, Nkx6.1, MafA or NeuroD1 (FIG. 5A, right). However, the levels of some of the transcriptional repressors examined—Stx3, Hes1, Crem, Insm1, Sox6, Tle4 and Bhlhe22—showed a significant increase (FIG. 5A, left). Over-expression of the repressors Sox6 and Bhlhe22 in the HIT beta-cell line caused a reduction in insulin expression which was measured by the reduction in luciferase activity driven by the RIP1 promoter. **p<0.01.

Figure 6A:
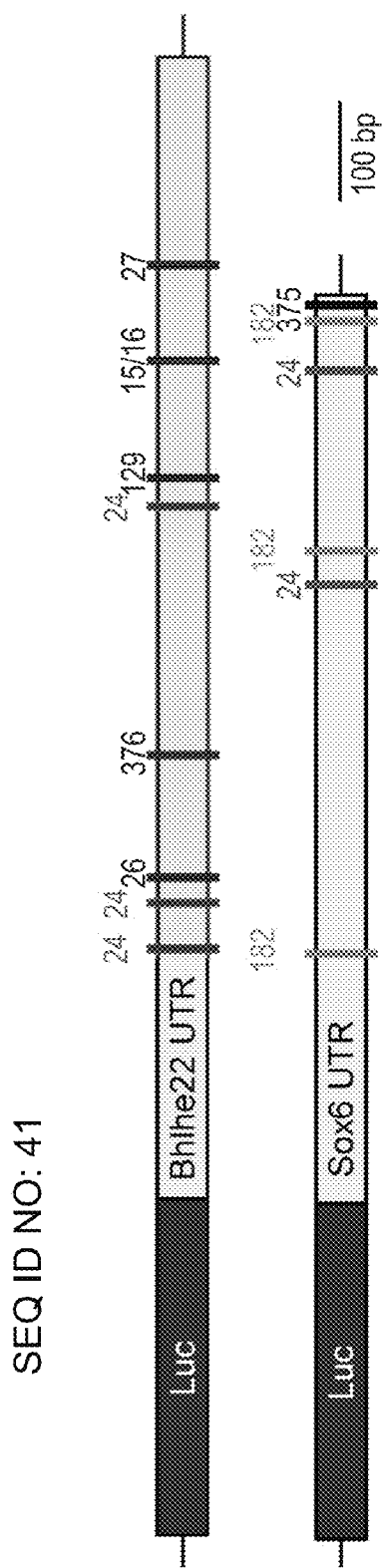
Figure 6B:
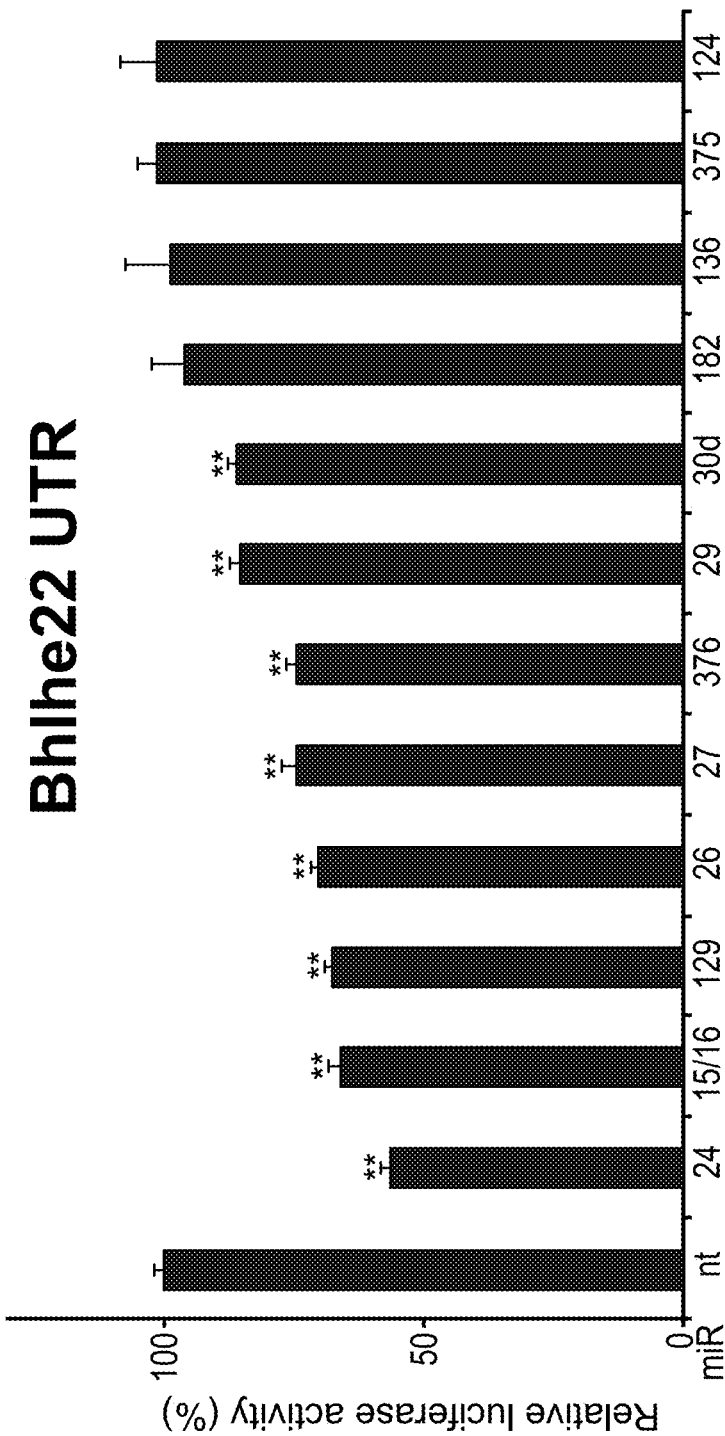
Figure 6C:
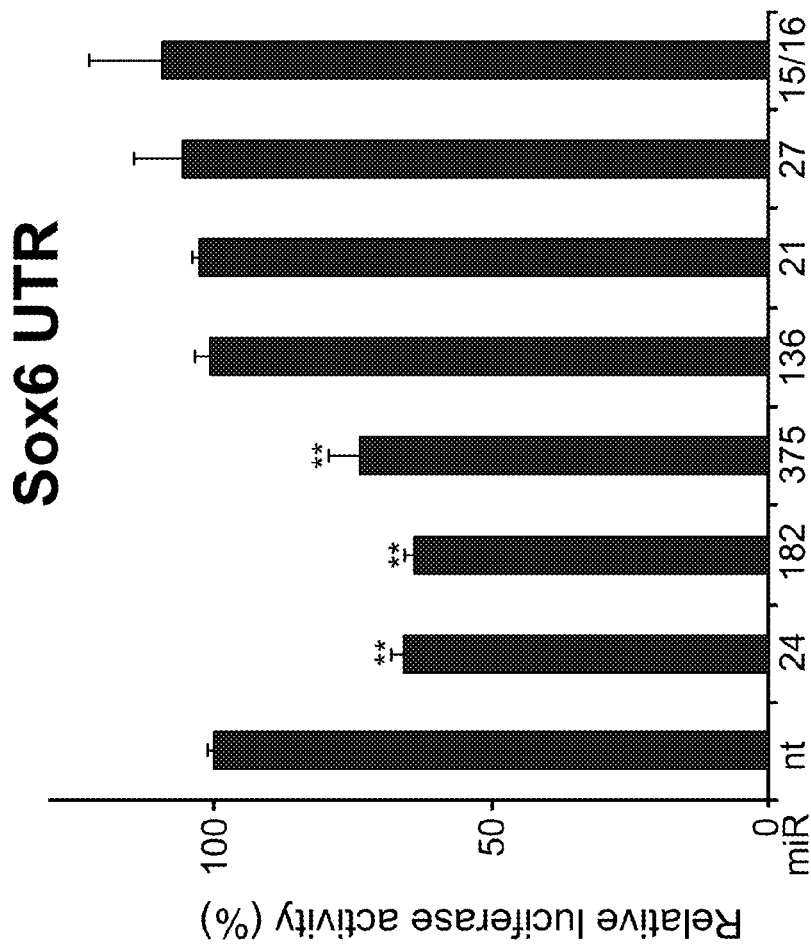

FIGS. 6A-C depict repressed Sox6 or Bhlhe22 expression by a few miRNAs. FIG. 6A depicts a schematic representation of the constructs containing luciferase (luc) sequences fused to the 3'UTR sequences of Sox6 and Bhlhe22 (SEQ ID NOs: 42 and 41, respectively). Vertical bars mark the location of predicted target sites of the miRNAs that affect luciferase expression. These constructs were co-transfected with various miRNA expression constructs predicted to target these UTRs. The expression of only a few of the miRNAs causes a reduction in luciferase activity driven by the Bhlhe22 (FIG. 6B) or Sox6 UTR (FIG. 6C). The bars represent % luciferase activity relative to a non-targeting (nt) control miRNA. Values shown are mean±SEM. * p<0.05, **p<0.01.

FIGS. 7A-F depict βDc$^{null}$ beta cells maintain normal PC1/3 expression. Immunostaining of PC1/3 (FIGS. 7B and 7E) and GFP expression (FIGS. 7A and 7D) showed their co-localization in the merged picture (FIGS. 7C and 7F, yellow) in both βDc$^{null}$ (FIGS. 7D-F) and control (FIGS. 7A-C) animals.

DESCRIPTION OF SPECIFIC EMBODIMENTS OF THE INVENTION

The present invention, in some embodiments thereof, relates to microRNAs, more particularly, but not exclusively, to expression or repression of same in pancreatic beta cells for modulation of insulin levels.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have uncovered that insulin levels may be modified in pancreatic beta cells by modulation of microRNAs.

As is illustrated hereinbelow and in the Examples section which follows the present inventors have uncovered that down-regulation of microRNAs leads to a significant decrease in insulin levels in pancreatic beta cells. Specifically, the present inventors have shown that depletion in the microRNA processing enzyme, Dicer1, in adult beta cells causes overt diabetes in mice (βDc$^{null}$ mice, see Example 1). The diabetes in these mice was not caused by loss of beta cell mass but rather by a decrease in insulin levels in the pancreatic beta cells (see Example 2). Further research showed a significant loss of transcriptional activity in the insulin promoter in the Dicer1 mutant cells (see Example 3) which was accompanied by an abnormal upregulation in transcriptional repressors (e.g. Sox6 and Bhlhe22, see Example 5). Moreover, the present inventors have uncovered that specific microRNAs (e.g. miR-24, miR-129, miR-15/16, miR-26, miR-27, miR182 and miR-375) are capable of binding and repressing the transcriptional repressors (see Example 6), thus, allowing reactivation of insulin transcription. The present inventors conclude that modulation of microRNAs may be used to activate or repress the Insulin 1 and Insulin 2 genes in pancreatic beta cells.

Thus, according to one aspect of the present invention there is provided a method of increasing insulin content in a pancreatic beta cell, the method comprising expressing in the pancreatic beta cell an exogenous polynucleotide encoding at least one microRNA or a precursor thereof thereby increasing the insulin content in the pancreatic beta cell.

According to a specific embodiment, the microRNA of the present invention may comprise miR-15, miR-16, miR-24, miR-26a,b, miR-27a,b, miR-29, miR-30a,b,c,d,e, miR-129, miR-141, miR-148a,b, miR-182, miR-200a,b,c, miR-376 and/or Let7a,b,c,d,e,f,g,i.

The phrase "pancreatic beta cell" as used herein refers to pancreatic islet endocrine cells which are capable of secreting insulin in response to elevated glucose concentrations and express typical beta cell markers. Examples of beta cell markers include, but are not limited to, insulin, pdx, Hnf313, PC1/3, Beta2, Nkx2.2, GLUT2 and PC2.

According to the present teachings, the pancreatic beta cell may be part of a tissue (e.g. within a body) or may comprise isolated cells. The isolated pancreatic beta cells may be of homogeneous or heterogeneous nature. Thus, for example, the pancreatic beta cells may be comprised in isolated pancreatic islets. Islet cells are typically comprised of the following: 1) beta cells that produce insulin; 2) alpha cells that produce glucagon; 3) delta cells (or D cells) that produce somatostatin; and/or F cells that produce pancreatic polypeptide. The polypeptide hormones (insulin, glucagon, somatostatin and pancreatic polypeptide) inside these cells are stored in secretary vesicles in the form of secretory granules.

Methods of isolating islets are well known in the art. For example, islets may be isolated from pancreatic tissue using collagenase and ficoll gradients. An exemplary method is described in U.S. Patent Application No. 20080014182, incorporated herein by reference.

It will be appreciated that depending on the intended use of the beta cells (explained in further detail, hereinbelow), the pancreatic beta cells may be isolated from the islets (e.g. by FACS sorting), may be dispersed into a single cell suspension (e.g. by the addition of trypsin or by trituration) and/or may be cultured (e.g. in cell medium such as CMRL-1066, available from e.g. Cellgro, Mediatech, Inc.). Thus, expressing microRNAs in pancreatic beta cells may be effected in vivo, ex vivo or in vitro.

As used herein, the phrase "insulin content" refers to the amount of mature insulin inside a pancreatic beta cell.

According to the present teachings, microRNA expression in a pancreatic beta cell results in an increase in insulin content as a result of an increase in insulin transcription and/or post transcriptional control and/or increase in insulin translation and/or post-translational control. The increase in insulin content in the pancreatic beta cell according to the present teachings may also result from enhanced insulin storage and/or retarding insulin breakdown.

Measurement of insulin content is well known in the art. An exemplary method is extraction of cellular insulin with 3 M acetic acid. The amount of mature insulin extracted from the pancreatic beta cell may be determined using an ELISA kit commercially available from e.g. Mercodia, Uppsala, Sweden.

As used herein, the term "microRNA or a precursor thereof" refers to the microRNA (miRNA) molecules acting as post-transcriptional regulators. MicroRNAs are typically processed from pre-miR (pre-microRNA precursors). Pre-miRs are a set of precursor miRNA molecules transcribed by RNA polymerase III that are efficiently processed into functional miRNAs, e.g., upon transfection into cultured cells. A Pre-miR can be used to elicit specific miRNA activity in cell types that do not normally express this miRNA, thus addressing the function of its target by down regulating its expression in a "gain of (miRNA) function" experiment. Pre-miR designs exist to all of the known miRNAs listed in the miRNA Registry and can be readily designed for any research.

It will be appreciated that the microRNAs of the present teachings may bind, attach, regulate, process, interfere, augment, stabilize and/or destabilize any microRNA target. Such a target can be any molecule, including, but not limited to, DNA molecules, RNA molecules and polypeptides, such as but not limited to, transcriptional repressors (e.g. Sox6, Bhlhe22, Crem, Insm1 and Tle4).

It will be appreciated that the microRNAs of the present invention are part of, involved in and/or are associated with an insulin transcription pathway. Such a microRNA can be identified via various databases including for example the microRNA registry (http://wwwdotsangerdotacdotuk/Software/Rfam/mirna/indexdotshtml).

Thus, according to the present teachings, the insulin content within a pancreatic beta cell may be increased (e.g. upregulated) by expression of a microRNA polynucleotide.

The term "polynucleotide" refers to a single-stranded or double-stranded oligomer or polymer of ribonucleic acid (RNA), deoxyribonucleic acid (DNA) or mimetics thereof. This term includes polynucleotides and/or oligonucleotides derived from naturally occurring nucleic acids molecules (e.g., RNA or DNA), synthetic polynucleotide and/or oligonucleotide molecules composed of naturally occurring bases, sugars, and covalent internucleoside linkages (e.g., backbone), as well as synthetic polynucleotides and/or oligonucleotides having non-naturally occurring portions, which function similarly to respective naturally occurring portions.

The length of the polynucleotide of the present invention is optionally of 100 nucleotides or less, optionally of 90 nucleotides or less, optionally 80 nucleotides or less, optionally 70 nucleotides or less, optionally 60 nucleotides or less, optionally 50 nucleotides or less, optionally 40 nucleotides or less, optionally 30 nucleotides or less, e.g., 29 nucleotides, 28 nucleotides, 27 nucleotides, 26 nucleotides, 25 nucleotides, 24 nucleotides, 23 nucleotides, 22 nucleotides, 21 nucleotides, 20 nucleotides, 19 nucleotides, 18 nucleotides, 17 nucleotides, 16 nucleotides, 15 nucleotides, optionally between 12 and 24 nucleotides, optionally between 5-15, optionally, between 5-25, most preferably, about 20-25 nucleotides.

The polynucleotides (including oligonucleotides) designed according to the teachings of the present invention can be generated according to any oligonucleotide synthesis method known in the art, including both enzymatic syntheses or solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

It will be appreciated that a polynucleotide comprising an RNA molecule can be also generated using an expression vector as is further described hereinbelow.

Preferably, the polynucleotide of the present invention is a modified polynucleotide. Polynucleotides can be modified using various methods known in the art.

For example, the oligonucleotides or polynucleotides of the present invention may comprise heterocylic nucleosides consisting of purines and the pyrimidines bases, bonded in a 3'-to-5' phosphodiester linkage.

Preferably used oligonucleotides or polynucleotides are those modified either in backbone, internucleoside linkages, or bases, as is broadly described hereinunder.

Specific examples of preferred oligonucleotides or polynucleotides useful according to this aspect of the present invention include oligonucleotides or polynucleotides containing modified backbones or non-natural internucleoside linkages. Oligonucleotides or polynucleotides having modified backbones include those that retain a phosphorus atom in the backbone, as disclosed in U.S. Pat. Nos. 4,469,863; 4,476, 301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide or polynucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide or polynucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides or polynucleotides which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Oligonucleotides or polynucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

According to a specific embodiment, upregulating the function of the miRNA of the present invention is effected using a polynucleotide having a nucleic acid sequence as set forth in SEQ ID NOs: 43-56 and 59-72 (see Table 1).

TABLE 1 miRNA polynucleotide sequences

| miRNA | Sequence: |
|---|---|
| miR-30 | uguaaacauccucgacuggaag (SEQ ID NO: 43) |
|  | uguaaacauccuugacuggaag (SEQ ID NO: 44) |
|  | uguaaacaucccgacuggaag (SEQ ID NO: 45) |
| miR-200/ 141 | uaauacugccggguaaugaugga (SEQ ID NO: 46) |
|  | uaauacugccugguaaugauga (SEQ ID NO: 47) |
|  | uaacacugucgguaaagaugg (SEQ ID NO: 48) |
|  | uaacacugucgguaacgaugu (SEQ ID NO: 49) |
| miR-24 | uggcucaguucagcaggaacag (SEQ ID NO: 50) |
| miR-27 | uucacaguggcuaaguucugc (SEQ ID NO: 51) |
| Let-7 | ugagguaguagguuguaugguu (SEQ ID NO: 52) |
|  | ugagguaguagguuguauaguu (SEQ ID NO: 53) |
|  | ugagguaguagguuguguggu (SEQ ID NO: 54) |
|  | ugagguaguagauuguauaguu (SEQ ID NO: 55) |
|  | ugagguaggagguuguauaguu (SEQ ID NO: 56) |
| miR-375 | uuuguucguucggcucgcguga (SEQ ID NO: 59) |
| miR-148 | ucagugcacuacagaacuuugu (SEQ ID NO: 60) |
|  | ucagugcaucacagaacuuugu (SEQ ID NO: 61) |
| miR-26 | uucaaguaauccaggauaggcu (SEQ ID NO: 62) |
|  | uucaaguaauucaggauaggu (SEQ ID NO: 63) |
| miR-182 | uuuggcaaugguagaacucacaccg (SEQ ID NO: 64) |
| miR-376 | aacauagaggaaauuucacgu (SEQ ID NO: 65) |
|  | uggaagacuagugauuuuguugu (SEQ ID NO: 66) |
|  | uggaagacuugugauuuuguugu (SEQ ID NO: 67) |
|  | uagcagcacaucaugguuuaca (SEQ ID NO: 68) |
| miR-15 | uagcagcacguaaauauuggcg (SEQ ID NO: 69) |
| miR-16 | uagcaccauuugaaaucaguguu (SEQ ID NO: 70) |
| miR-29 | uagcaccaucugaaaucgguua (SEQ ID NO: 71) |
| miR-129 | cuuuuugcggucugggcuugc (SEQ ID NO: 72) |

As is mentioned hereinabove and is shown in the Examples section which follows, micro-RNAs are processed molecules derived from specific precursors (i.e., pre-miRNA), upregulation of a specific miRNA function can be effected using a specific miRNA precursor molecule.

Polynucleotide agents for up-regulating microRNA expression in pancreatic beta cells may be provided to the pancreatic beta cells per se. Such polynucleotide agents are typically administered to the pancreatic beta cells as part of an expression construct. In this case, the polynucleotide agent is ligated in a nucleic acid construct under the control of a cis-acting regulatory element (e.g. promoter) capable of directing an expression of the microRNA in the pancreatic beta cells in a constitutive or inducible manner.

Examples of microRNA polynucleotide agents of the present invention include, but are not limited to, miR-15 (e.g. GenBank accession no. NR_029485 RNA), miR-16 (e.g. GenBank accession no. NR_029486), miR-24 (e.g. GenBank accession nos. NR_029496 and NR_029497), miR-26 (e.g. GenBank accession no. NR_029500 and NR_029499), miR-27 (e.g. GenBank accession no. NR_029501 RNA), miR-29 (e.g. GenBank accession no. NR_029503 and NR_029832), miR-129 (e.g. GenBank accession nos. NR_029596 and NR_029697) and miR-182 (e.g. GenBank accession no. NR_029614).

Examples of B cell specific promoters include, but are not limited to the insulin promoter, Nkx6.1 promoter, Nkx2.2 promoter, IPF-1 promoter, Pdx1 promoter and beta-cell glucokinase (GCK) promoter.

The expression constructs of the present invention may also include additional sequences which render it suitable for replication and integration in eukaryotes (e.g., shuttle vectors). Typical cloning vectors contain transcription and translation initiation sequences (e.g., promoters, enhances) and transcription and translation terminators (e.g., polyadenylation signals). The expression constructs of the present invention can further include an enhancer, which can be adjacent or distant to the promoter sequence and can function in up regulating the transcription therefrom.

Enhancer elements can stimulate transcription up to 1.000-fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus or human or murine cytomegalovirus (CMV) and the long tandem repeats (LTRs) from various retroviruses, such as murine leukemia virus, murine or Rous sarcoma virus, and HIV. See Gluzman, Y. and Shenk, T., eds. (1983). Enhancers and Eukaryotic Gene Expression, Cold Spring Harbor Press, Cold Spring Harbor, N.Y., which is incorporated herein by reference.

Polyadenylation sequences can also be added to the expression constructs of the present invention in order to increase the efficiency of expression of the detectable moeity. Two distinct sequence elements are required for accurate and efficient polyadenylation: GU- or U-rich sequences located downstream from the polyadenylation site and a highly conserved sequence of six nucleotides, namely AAUAAA, located 11-30 nucleotides upstream of the site. Termination and polyadenylation signals suitable for the present invention include those derived from SV40.

In addition to the embodiments already described, the expression constructs of the present invention may typically contain other specialized elements intended to increase the level of expression of cloned nucleic acids or to facilitate the identification of cells that carry the recombinant DNA. For example, a number of animal viruses contain DNA sequences that promote extra-chromosomal replication of the viral genome in permissive cell types. Plasmids bearing these viral replicons are replicated episomally as long as the appropriate factors are provided by genes either carried on the plasmid or with the genome of the host cell.

The expression constructs of the present invention may or may not include a eukaryotic replicon. If a eukaryotic replicon is present, the vector is capable of amplification in eukaryotic cells using the appropriate selectable marker. If the construct does not comprise a eukaryotic replicon, no episomal amplification is possible. Instead, the recombinant DNA integrates into the genome of the engineered cell, where the promoter directs expression of the desired nucleic acid.

The nucleic acid construct may be introduced into the pancreatic beta cells of the present invention using an appropriate gene delivery vehicle/method (transfection, transduction, etc.) and an appropriate expression system.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, and pNMT81, which are available from Invitrogen, pCI which is available from Promega, pMbac, pPbac, pBK-RSV and pBK-CMV, which are available from Stratagene, pTRES which is available from Clontech, and their derivatives.

Expression vectors containing regulatory elements from eukaryotic viruses such as retroviruses can be also used. SV40 vectors include pSVT7 and pMT2, for instance. Vectors derived from bovine papilloma virus include pBV-1MTHA, and vectors derived from Epstein-Ban virus include pHEBO and p205. Other exemplary vectors include pMSG, pAV009/A+, pMTO10/A+, pMAMneo-5 and baculovirus pDSVE.

Lipid-based systems may be used for the delivery of these constructs into the pancreatic beta cells of the present invention. Useful lipids for lipid-mediated transfer of the gene are, for example, DOTMA, DOPE, and DC-Chol [Tonkinson et al., Cancer Investigation, 14(1): 54-65 (1996)]. Recently, it has been shown that Chitosan can be used to deliver nucleic acids to the intestine cells (Chen J. (2004) World J Gastroenterol 10(1):112-116). Other non-lipid based vectors that can be used according to this aspect of the present invention include but are not limited to polylysine and dendrimers.

The expression construct may also be a virus. Examples of viral constructs include but are not limited to adenoviral vectors, retroviral vectors, vaccinia viral vectors, adeno-associated viral vectors, polyoma viral vectors, alphaviral vectors, rhabdoviral vectors, lenti viral vectors and herpesviral vectors.

Retroviral vectors represent a class of vectors particularly suitable for use with the present invention. Defective retroviruses are routinely used in transfer of genes into mammalian cells (for a review, see Miller, A. D. (1990). Blood 76, 271). A recombinant retrovirus comprising the polynucleotides of the present invention can be constructed using well-known molecular techniques. Portions of the retroviral genome can be removed to render the retrovirus replication machinery defective, and the replication-deficient retrovirus can then packaged into virions, which can be used to infect target cells through the use of a helper virus while employing standard techniques. Protocols for producing recombinant retroviruses and for infecting cells with viruses in vitro or in vivo can be found in, for example, Ausubel et al. (1994) Current Protocols in Molecular Biology (Greene Publishing Associates, Inc. & John Wiley & Sons, Inc.). Retroviruses have been used to introduce a variety of genes into many different cell types, including neuronal cells, epithelial cells, endothelial cells, lymphocytes, myoblasts, hepatocytes, and bone marrow cells.

According to one embodiment, a lentiviral vector, a type of retroviral vector, is used according to the present teachings. Lentiviral vectors are widely used as vectors due to their ability to integrate into the genome of non-dividing as well as dividing cells. The viral genome, in the form of RNA, is reverse-transcribed when the virus enters the cell to produce DNA, which is then inserted into the genome at a random position by the viral integrase enzyme. The vector (a provirus) remains in the genome and is passed on to the progeny of the cell when it divides. For safety reasons, lentiviral vectors never carry the genes required for their replication. To produce a lentivirus, several plasmids are transfected into a so-called packaging cell line, commonly HEK 293. One or more plasmids, generally referred to as packaging plasmids, encode the virion proteins, such as the capsid and the reverse transcriptase. Another plasmid contains the genetic material to be delivered by the vector. It is transcribed to produce the single-stranded RNA viral genome and is marked by the presence of the ψ (psi) sequence. This sequence is used to package the genome into the virion.

A specific example of a suitable lentiviral vector for introducing and expressing the polynucleotide sequences of the present invention in beta cells is the lentivirus pLKO.1 vector.

Another suitable expression vector that may be used according to this aspect of the present invention is the adenovirus vector. The adenovirus is an extensively studied and routinely used gene transfer vector. Key advantages of an adenovirus vector include relatively high transduction efficiency of dividing and quiescent cells, natural tropism to a wide range of epithelial tissues, and easy production of high titers (Russel, W. C. (2000) J Gen Virol 81, 57-63). The adenovirus DNA is transported to the nucleus, but does not integrate thereinto. Thus the risk of mutagenesis with adenoviral vectors is minimized, while short-term expression is particularly suitable for treating cancer cells. Adenoviral vectors used in experimental cancer treatments are described by Seth et al. (1999). "Adenoviral vectors for cancer gene therapy," pp. 103-120, P. Seth, ed., Adenoviruses: Basic Biology to Gene Therapy, Landes, Austin, Tex.).

A suitable viral expression vector may also be a chimeric adenovirus/retrovirus vector combining retroviral and adenoviral components. Such vectors may be more efficient than traditional expression vectors for transducing tumor cells (Pan et al. (2002). Cancer Letts 184, 179-188).

Various methods can be used to introduce the expression vectors of the present invention into human cells. Such methods are generally described in, for instance: Sambrook, J. and Russell, D. W. (1989, 1992, 2001), Molecular Cloning: A Laboratory Manual, Cold Springs Harbor Laboratory, New York; Ausubel, R. M. et al., eds. (1994, 1989). Current Protocols in Molecular Biology, John Wiley and Sons, Baltimore, Md. (1989); Chang, P. L., ed. (1995). Somatic Gene Therapy, CRC Press, Boca Raton, Fla.; Vega, M. A. (1995). Gene Targeting, CRC Press, Boca Raton, Fla.; Rodriguez, R. L. and Denhardt, D. H. (1987). Vectors: A Survey of Molecular Cloning Vectors and Their Uses, Butterworth-Heinemann, Boston, Mass.; and Gilboa, E. et al. (1986). Transfer and expression of cloned genes using retro-viral vectors. Biotechniques 4(6), 504-512; and include, for example, stable or transient transfection, lipofection, electroporation, and infection with recombinant viral vectors. In addition, see U.S. Pat. Nos. 5,464,764 and 5,487,992 for positive-negative selection methods.

When introducing the expression constructs of the present invention into beta cells by viral infection the viral dose for infection is at least $10^3$, $10^4$, $10^5$, $10^6$, $10^7$, $10^8$, $10^9$, $10^{10}$, $10^{11}$, $10^{12}$, $10^{13}$, $10^{14}$, $10^{15}$ or higher pfu or viral particles.

According to an embodiment of the present invention, there is provided an isolated pancreatic beta cell comprising the nucleic acid construct encoding a microRNA, as detailed above.

As mentioned the pancreatic beta cells of the present invention can be treated in vivo (i.e., inside the organism or the subject) or ex vivo (e.g., in a tissue culture). In case the cells are treated ex vivo, the method preferably includes a step of administering such cells back to the individual (ex vivo cell therapy). In vivo and ex vivo therapies are further discussed hereinbelow.

As mentioned, the present invention is based on the finding that downregulation of microRNA expression levels in pancreatic beta cells results in decreased insulin levels. As such, the present invention also contemplates decreasing (e.g. downregulating) microRNA levels in pancreatic beta cells in order to decrease insulin content in pancreatic cells.

Downregulation of microRNAs can be effected on the genomic and/or the transcript level using a variety of molecules which interfere with transcription and/or translation (e.g., RNA silencing agents, Ribozyme, DNAzyme and antisense), or on the protein level using e.g., antagonists, enzymes that cleave the polypeptide and the like.

Following is a list of agents capable of downregulating expression level and/or activity of microRNAs.

Downregulation of microRNAs can be achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, the present invention contemplates use of dsRNA to down-regulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl. Acad. Sci. USA. 2002; 99:1443-1448; Tran N., et al., FEBS Lett. 2004; 573: 127-134].

In particular, the present invention also contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The present invention also contemplates introduction of long dsRNA specifically designed not to induce the interferon and PKR pathways for down-regulating gene expression. For example, Shinagwa and Ishii [Genes & Dev. 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of the present invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

According to another embodiment the RNA silencing agent may be a miRNA. miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA (the strand that will eventually basepair with the target) The pre-miRNA is a substrate for a form of dicer that removes the miRNA duplex from the precursor, after which, similarly to siRNAs, the duplex can be taken into the RISC complex. It has been demonstrated that miRNAs can be transgenically expressed and be effective through expression of a precursor form, rather than the entire primary form (Parizotto et al. (2004) Genes & Development 18:2237-2242 and Guo et al. (2005) Plant Cell 17:1376-1386).

Unlike, siRNAs, miRNAs bind to transcript sequences with only partial complementarity (Zeng et al., 2002, Molec. Cell 9:1327-1333) and repress translation without affecting steady-state RNA levels (Lee et al., 1993, Cell 75:843-854; Wightman et al., 1993, Cell 75:855-862). Both miRNAs and siRNAs are processed by Dicer and associate with components of the RNA-induced silencing complex (Hutvagner et al., 2001, Science 293:834-838; Grishok et al., 2001, Cell 106: 23-34; Ketting et al., 2001, Genes Dev. 15:2654-2659; Williams et al., 2002, Proc. Natl. Acad. Sci. USA 99:6889-6894; Hammond et al., 2001, Science 293:1146-1150; Mourlatos et al., 2002, Genes Dev. 16:720-728). A recent report (Hutvagner et al., 2002, Sciencexpress 297:2056-2060) hypothesizes that gene regulation through the miRNA pathway versus the siRNA pathway is determined solely by the degree of complementarity to the target transcript. It is speculated that siRNAs with only partial identity to the mRNA target will function in translational repression, similar to an miRNA, rather than triggering RNA degradation.

Synthesis of RNA silencing agents suitable for use with the present invention can be effected as follows. First, the microRNA mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (wwwdotambiondotcom/techlib/tn/91/912dothtml).

Second, potential target sites are compared to an appropriate genomic database (e.g., human, mouse, rat etc.) using any sequence alignment software, such as the BLAST software available from the NCBI server (wwwdotncbidotnlmdot nih-dotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

It will be appreciated that the RNA silencing agent of the present invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of the present invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of the present invention preferably include, but are not limited to, penetratin, transportan, pIsl, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of the present invention may be targeted to a bridging region on either side of the deletion. Introduction of such RNA silencing agents into a cell would cause a down-regulation of the mutated protein while leaving the non-mutated protein unaffected. Exemplary microRNA silencing agents include, but are not limited to, Anti-miR™ miRNA Inhibitors available from Ambion Inc. for inhibition of miR-15, miR-16, miR-24, miR-26, miR-27, miR-29, miR-30d, miR-129 and miR-182 (for more details see https://productsdotappliedbiosystems-dotcom/ab/en/US/adirect/ab?cmd=ABAntiPremiR NAKeywordSearch).

Another agent capable of downregulating a microRNA is a DNAzyme molecule capable of specifically cleaving an mRNA transcript or DNA sequence of the microRNA. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther wwwdotasgtdotorg). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of a microRNA can also be effected by using an antisense polynucleotide capable of specifically hybridizing with an mRNA transcript encoding the microRNA.

Design of antisense molecules which can be used to efficiently downregulate a microRNA must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

microRNA antisense agents include, but are not limited to, antisense molecules which target and inhibit miRNA (e.g. miR-15, miR-16) described in detail in Cheng A. M. et al., Nucleic Acids Research 2005 33(4):1290-1297, incorporated herein by reference, and anti-miRNA oligos available from e.g. IDT (Integrated DNA Technologies, Inc, Israel) and also available from Exicon (miRCURY LNA™ microRNA Inhibitors, for more details see http://wwwdotexiqondotcom/microrna-knockdown).

Another agent capable of downregulating a microRNA is a ribozyme molecule capable of specifically cleaving an mRNA transcript encoding a microRNA. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Ribozymes specific for targeting microRNAs can be designed as was previously described by Suryawanshi, H. et al. [Supplementary Material (ESI) for Molecular BioSystems, The Royal Society of Chemistry 2010, incorporated herein by reference].

An additional method of regulating the expression of a microRNA gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

| oligo  | 3'--A | G | G | T |
| duplex | 5'--A | G | C | T |
| duplex | 3'--T | C | G | A |

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the microRNA regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence- and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Another agent which can be used along with the present invention to downregulate microRNA is a molecule which prevents microRNA activation or substrate binding.

As is shown in FIG. 1C and is described in Example 1 of the Examples section which follows, the level of pancreatic beta cell microRNA was significantly decreased in Dicer1 depleted cells.

Thus, according to a specific embodiment of the present invention, downregulating the levels of microRNAs in pancreatic beta cells may be effected by expressing in these cells miRNA digestion enzymes, including but not limited to, Drosha (RNASEN, e.g. GenBank accession nos: NP_001093882.1 and NP_037367.3, SEQ ID NOs: 77 and 78, respectively), Dicer1 (e.g. GenBank accession nos: NP_085124.2 and NP_803187.1, SEQ ID NOs: 79 and 80, respectively), DGCR8 (e.g. GenBank accession nos: NP_073564.3 and NP_892029.2, SEQ ID NOs: 81 and 82, respectively), exportin 5 (e.g. GenBank accession nos: NP_004866.1 and NP_976035.1, SEQ ID NOs: 83 and 84, respectively), Argonaute1 (EIF2C1, e.g. GenBank accession no: NP_036331.1, SEQ ID NO: 85), Argonaute2 (EIF2C2 e.g. GenBank accession nos: NP_001158095.1 and NP_036286.2, SEQ ID NOs: 86 and 87, respectively), Argonaute3 (EIF2C3 e.g. GenBank accession nos: NP_079128.2 and NP_803171.1, SEQ ID NOs: 88 and 89, respectively), Argonaute4 (EIF2C4 e.g. GenBank accession no: NP_060099.2, SEQ ID NO: 90), smad4 (e.g. GenBank accession no: NP_005350.1, SEQ ID NO: 91), Ran (e.g. GenBank accession no: NP_006316.1, SEQ ID NO: 92), TUT4 (ZCCHC11 e.g. GenBank accession nos: NP_001009881.1 and NP_056084.1, SEQ ID NOs: 93 and 94, respectively) and/or TRBP/TARBP2 (e.g. NP_004169.3, NP_599150.1 and NP_599151.2, SEQ ID NOs: 95-97).

Preferably, the polynucleotide of the present invention is a modified polynucleotide. Polynucleotides can be modified using various methods known in the art.

For example, the oligonucleotides or polynucleotides of the present invention may comprise heterocylic nucleosides consisting of purines and the pyrimidines bases, bonded in a 3'-to-5' phosphodiester linkage.

Preferably used oligonucleotides or polynucleotides are those modified either in backbone, internucleoside linkages, or bases, as is broadly described hereinunder.

Specific examples of preferred oligonucleotides or polynucleotides useful according to this aspect of the present invention include oligonucleotides or polynucleotides containing modified backbones or non-natural internucleoside linkages. Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide or polynucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide or polynucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides or polynucleotides which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Oligonucleotides or polynucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

It will be appreciated that the microRNA antisense agents (e.g. anti-miRNA oligos) of the present invention may also comprise chemical modifications and/or the addition of moieties, e.g. a cholesterol moiety (e.g. antagomirs). Such molecules have been previously described in e.g. Krützfeldt J. et al., Nature (2005) 438:685-9.

Methods of in vivo and ex vivo (in vitro) expression in eukaryotic cells are described hereinabove.

As mentioned, the present inventors have shown that microRNA depletion in pancreatic beta cells leads to overt diabetes (see Example 1 in the Examples section which follows). Thus, upregulating microRNA levels may be beneficial in cases in which a subject endures an insulin deficiency while downregulating microRNA expression may be beneficial in cases in which a subject endures elevated insulin levels.

Thus, according to another aspect of the present invention there is provided a method of treating a condition associated with an insulin deficiency in a subject in need thereof.

The term "treating" refers to inhibiting or arresting the development of a disease, disorder or condition and/or causing the reduction, remission, or regression of a disease, disorder or condition or keeping a disease, disorder or medical condition from occurring in a subject who may be at risk for the disease disorder or condition, but has not yet been diagnosed as having the disease disorder or condition. Those of skill in the art will understand that various methodologies and assays can be used to assess the development of a disease, disorder or condition, and similarly, various methodologies and assays may be used to assess the reduction, remission or regression of a disease, disorder or condition.

As used herein, the term "subject" refers to an animal, preferably a mammal, most preferably a human being, including both young and old human beings of both sexes who suffer from or are predisposed to an insulin associated disorder.

Diseases or syndromes which are associated with an insulin deficiency include, but are not limited to, type 1 and type 2 diabetes mellitus, metabolic syndrome, type 1 and type 2 diabetes mellitus subtypes, insulin deficiency syndrome, maturity onset diabetes of the young (MODY 1-11), and permanent neonatal diabetes mellitus.

According to a specific embodiment of the present invention, the insulin deficiency comprises diabetes.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and displays, among other symptoms and signs, elevated blood glucose concentration, presence of glucose in the urine and excessive discharge of urine.

According to the present teachings, in order to treat the insulin deficiency, the subject is administered an agent capable of increasing miRNA levels e.g. a polynucleotide encoding a microRNA (as detailed in further detail hereinabove).

According to yet another aspect of the present invention there is provided a method of treating a condition associated with elevated insulin levels.

Diseases or syndromes which are associated with elevated insulin levels include, but are not limited to, hyperinsulinemia, hyperinsulinemic hypoglycemia, congenital hyperinsulinism, diffuse hyperinsulinism, insulinomas (i.e. insulin-secreting tumors e.g. islet cell adenoma or adenomatosis or islet cell carcinoma), adult nesidioblastosis, autoimmune insulin syndrome, noninsulinoma pancreatogenous hypoglycemia, reactive hypoglycemia (idiopathic postprandial syndrome), gastric dumping syndrome, drug induced hyperinsulinism and Hypoglycemia due to exogenous (injected) insulin.

According to the present teachings, in order to treat the elevated insulin levels, the subject is administered an agent capable of decreasing miRNA levels (e.g. an enzyme), such agents are detailed in further detail hereinabove.

For in vivo therapy, the agent (e.g., a polynucleotide encoding a microRNA) is administered to the subject as is or as part of a pharmaceutical composition (see further detail hereinbelow).

For ex vivo therapy, cells are preferably treated with the agent of the present invention (e.g., a polynucleotide encoding a microRNA), following which they are administered to the subject in need thereof.

Administration of the ex vivo treated cells of the present invention can be effected using any suitable route of introduction, such as intravenous, intraperitoneal, intra-kidney, intra-gastrointestinal track, subcutaneous, transcutaneous, intramuscular, intracutaneous, intrathecal, epidural, and rectal. According to presently preferred embodiments, the ex vivo treated cells of the present invention may be introduced to the individual using intravenous, intra-kidney, intra-gastrointestinal track, and/or intraperitoneal administration.

The pancreatic beta cells of the present invention can be derived from either autologous sources or from allogeneic sources such as human cadavers or donors. Since non-autologous cells are likely to induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles, and macroencapsulation, involving larger flat-sheet and hollow-fiber membranes (Uludag, H. et al. (2000). Technology of mammalian cell encapsulation. Adv Drug Deliv Rev 42, 29-64).

Methods of preparing microcapsules are known in the art and include for example those disclosed in: Lu, M. Z. et al. (2000). Cell encapsulation with alginate and alpha-phenoxy-cinnamylidene-acetylated poly(allylamine). Biotechnol Bioeng 70, 479-483; Chang, T. M. and Prakash, S. (2001) Procedures for microencapsulation of enzymes, cells and genetically engineered microorganisms. Mol Biotechnol 17, 249-260; and Lu, M. Z., et al. (2000). A novel cell encapsulation method using photosensitive poly(allylamine alpha-cyanocinnamylideneacetate). J Microencapsul 17, 245-521.

For example, microcapsules are prepared using modified collagen in a complex with a ter-polymer shell of 2-hydroxyethyl methylacrylate (HEMA), methacrylic acid (MAA), and methyl methacrylate (MMA), resulting in a capsule thickness of 2-5 μm. Such microcapsules can be further encapsulated with an additional 2-5 μm of ter-polymer shells in order to impart a negatively charged smooth surface and to minimize plasma protein absorption (Chia, S. M. et al. (2002). Multilayered microcapsules for cell encapsulation. Biomaterials 23, 849-856).

Other microcapsules are based on alginate, a marine polysaccharide (Sambanis, A. (2003). Encapsulated islets in diabetes treatment. Diabetes Thechnol Ther 5, 665-668), or its derivatives. For example, microcapsules can be prepared by the polyelectrolyte complexation between the polyanions sodium alginate and sodium cellulose sulphate and the polycation poly(methylene-co-guanidine) hydrochloride in the presence of calcium chloride.

It will be appreciated that cell encapsulation is improved when smaller capsules are used. Thus, for instance, the quality control, mechanical stability, diffusion properties, and in vitro activities of encapsulated cells improved when the capsule size was reduced from 1 mm to 400 µm (Canaple, L. et al. (2002). Improving cell encapsulation through size control. J Biomater Sci Polym Ed 13, 783-96). Moreover, nanoporous biocapsules with well-controlled pore size as small as 7 nm, tailored surface chemistries, and precise microarchitectures were found to successfully immunoisolate microenvironments for cells (See: Williams, D. (1999). Small is beautiful: microparticle and nanoparticle technology in medical devices. Med Device Technol 10, 6-9; and Desai, T. A. (2002). Microfabrication technology for pancreatic cell encapsulation. Expert Opin Biol Ther 2, 633-646).

Examples of immunosuppressive agents which may be used in conjunction with the ex vivo treatment include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE.sup.R), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

The microRNA polynucleotide, microRNA expression vector as well as the microRNA downregulating agent of the present invention can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (up-regulating or downregulating agent) effective to prevent, alleviate or ameliorate symptoms of a disorder (e.g., insulin related disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide ample levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc. The dosage and timing of administration will be responsive to a careful and continuous monitoring of the individual changing condition.

It will be appreciated that animal models exist by which the agents of the present invention may be tested prior to human treatment. For example, Type I diabetes models include, pancreatectomy in dogs, spontaneous rodent models (e.g. BBDP rats and the NOD mice). Type II diabetes models and obese animal models include, db/db (diabetic) mice, Zucker diabetic fatty (ZDF) rats, sand rats (*Psammomys obesus*) and obese rhesus monkeys.

Regardless of the above, the agents of the present invention are administered at an amount selected to avoid unwanted side-effects associated with elevated concentrations of microRNA.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The agents of the invention can be suitably formulated as pharmaceutical compositions which can be suitably packaged as an article of manufacture. Such an article of manufacture comprises a label for use in treating an insulin related disease (e.g. diabetes), the packaging material packaging a pharmaceutically effective amount of the microRNA upregulating or downregulating agent.

It will be appreciated that each of the agents or compositions of the present invention may be administered in combination with other known treatments, including but not limited to, insulin including short-acting insulin [e.g. lispro (Humalog) or aspart (NovoLog)] and longer acting insulin [e.g. Neutral Protamine Hagedorn (NPH), Lente, glargine (Lantus), detemir, or ultralente] and oral medication for control of blood sugar levels e.g. sulfonylurea or biguanide [metformin Glucophage)].

The agents or compositions of the present invention may be administered prior to, concomitantly with or following administration of the latter.

In order to test treatment efficacy, the subject may be evaluated by physical examination as well as using any method known in the art, as for example, by finger stick blood glucose test, fasting plasma glucose test, oral glucose tolerance test, glycosylated hemoglobin or hemoglobin A1c, body mass index (BMI) and the like.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Procedures

Mouse Strains

Mice were housed and handled in accordance with protocols approved by the Institutional Animal Care and Use Committee of WIS. Mouse strains which were used herein: Insulin-CreER [previously described in Dor, Y. et al. (2004) Nature 429, 41-46], Dicer1$^{floxed}$ [previously described in Harfe, B. D. et al. (2005) Proc Natl Acad Sci USA 102, 10898-10903] and Z/EG [previously described in Novak, A. et al. (2000) Genesis 28, 147-155]. Transgenic mice were genotyped by PCR on tail DNA extracted using DirectPCR (Viagen). The following primers were used: Dicer1 forward: CCTGACAGTGACGGTCCAAAG (SEQ ID NO: 1), Dicer1 reverse: CATGACTCTTCA-ACTCAAACT (SEQ ID NO: 2), Cre forward: TGCCACGACCAAGTGACAGC (SEQ ID NO: 3), Cre reverse: CCAGGTTACGGATATAGTTCATG (SEQ ID NO: 4), GFP forward: CCTACGGCGTG-CAGTGC-TTCAGC (SEQ ID NO: 5) and GFP reverse: CGGCGAGCTGCACGCT-GCGTCCTC (SEQ ID NO: 6). Tamoxifen (Sigma-Aldrich) was dissolved in corn oil to 20 mg/ml. 5 doses of 8 mg Tamoxifen were injected subcutaneously every other day over 10 days to 1-5 month old Rip-Cre-ER;Dicer1 animals.

Pancreas Physiology Assays

Blood glucose was determined using an 'Acsensia elite' glucometer. Pancreatic insulin content and serum insulin levels were determined using an ultrasensitive rat insulin ELISA kit (Crystal Chem). Glucose tolerance tests were performed by injecting glucose (2 mg/kg) intraperitoneally after overnight fasting.

Pancreatic Histology and Immunohistochemistry

Pancreata were dissected and fixed in 4% paraformaldehyde for 24 h at room temperature and then processed into paraffin blocks. 3-5 µm thick sections were de-paraffinized, rehydrated and subjected to antigen retrieval in a 2100-Retriever (PickCell Laboratories, The Netherlands). The following primary antibodies were used: guinea pig anti-insulin (1:200; DAKO), rabbit anti-glucagon (1:200; DAKO), rabbit anti-somatostatin (1:200; Zymed), goat anti-GFP (1:100; Abcam), rabbit anti-GFP (1:250; Invitrogen), rabbit anti-Pdx1 (1:5000; Beta Cell Biology Consortium), Rabbit anti-Ngn3 (1:300; Santa Cruz), mouse anti-Nkx6.1 (1:100; hybridoma bank), Rabbit anti-mafA (1:100, Bethyl), Rabbit anti-synaptophysin (1:100; DAKO), Rabbit anti-Pax6 (1:300; Chemicon), Goat anti-ghrelin (1:50; Santa Cruz), rabbit anti-activated caspase-3 (1:50, cell signaling) and rabbit anti-prohormone convertase 1/3 (1:100; Chemicon). Secondary antibodies conjugated to CY2, CY3, or CY5 were all from Jackson Immunoresearch Laboratories (1:100). Insulin immunohistochemistry was conducted with a secondary antibody conjugated to biotin (Jackson Immunoresearch Laboratories) followed by incubation with extravidin-HRP (Sigma) and developed using a DAB substrate kit (Zymed laboratories). Hoechst (Sigma) was used for nuclear counterstain (1 µg/ml). Fluorescence images were captured using a Zeiss LSM510 Laser Scanning/confocal microscope system equipped with a Zeiss camera under a magnification of ×40.

Islet Isolation

Islets were isolated from whole pancreata as was previously described by Lacy and Kostianovsky [Lacy, P. E. and Kostianovsky, M. (1967) Diabetes 16, 35-39]. Upon laparotomy, the pancreatic duct was identified and retrograde intraductal perfusion of 0.166 mg/ml liberase RI or TM (Roche) diluted in Hank's Balanced Salt Solution (Sigma-Aldrich) supplemented with 1.5 mg/ml DNaseI (Roche) was performed through the sphincter of oddi. Islets were hand-picked and frozen in liquid nitrogen.

RNA Quantification by qPCR

Islet RNA was extracted using RNeasy or miRNeasy kit (Qiagen) following the manufacturer's instructions. The RNA samples were DNase-I treated on column (Qiagen). cDNA synthesis was carried out using an oligo d(T) primer (Promega) and SuperScript II reverse transcriptase (Invitrogen) following the manufacturer's instructions on 100-500 ng islet RNA. qPCR analysis of mRNA expression was performed using DyNAmo™ SYBR® Green qPCR kit (Finnzymes) following the manufacturer's instructions. GAPDH and HPRT were used as control reference genes for normalization. All the qPCR reactions were done in a Light-Cycler® 480 Real-Time PCR System (Roche). All of the primers used for qPCR are detailed in Table 2, below.

TABLE 2

Primers for quantitative real-time PCR of mRNAs

| Gene | Forward primer | Reverse primer |
|---|---|---|
| Dicer1 | CACGCCTCCTACCACTACAACA (SEQ ID NO. 7) | CCTGGAGAATGCTGCCGTGGGT (SEQ ID NO. 8) |
| Insulin1 | CCTGTTGGTGCACTTCCTAC (SEQ ID NO. 9) | TGCAGTAGTTCTCCAGCTGG (SEQ ID NO. 10) |
| Insulin2 | CGTGGCTTCTTCTACACACCC (SEQ ID NO. 11) | AGCTCCAGTTGTGCCACTTGT (SEQ ID NO. 12) |
| Pdx1 | TTCCCGAATGGAACCGAGC (SEQ ID NO. 13) | GTAGGCAGTACGGGTCCTCT (SEQ ID NO. 14) |
| Nkx2.2 | CCGGGCGGAGAAAGGTATG (SEQ ID NO. 15) | CTGTAGGCGGAAAAGGGGA (SEQ ID NO. 16) |
| Nkx6.1 | TCAGTCAAGGTCTGGTTCC (SEQ ID NO. 17) | CGATTTGTGCTTTTTCAGCA (SEQ ID NO. 18) |
| MafA | AGGAGGAGGTCATCCGACTG (SEQ ID NO. 19) | CTTCTCGCTCTCCAGAATGTG (SEQ ID NO. 20) |

TABLE 2-continued

Primers for quantitative real-time PCR of mRNAs

| Gene | Forward primer | Reverse primer |
|---|---|---|
| NeouroD1 | GACCCAGAAACTGTCTAAAATAGAGACA (SEQ ID NO. 21) | AAGGAGACCAGATCAGGGCTTT (SEQ ID NO. 22) |
| Stx3 | GAAGGCACGGGATGAAACTAA (SEQ ID NO. 23) | GGACAGTCCAATAATCAACGCTA (SEQ ID NO. 24) |
| Hes1 | GTCTAAGCCAACTGAAAACACTGATT (SEQ ID NO. 25) | TGCCTTCTCTAGCTTGGAATGC (SEQ ID NO. 26) |
| Insm1 | CGGCCACCTTCTACAGCTC (SEQ ID NO. 27) | GGAGGATCACCTGTCTATTCTCA (SEQ ID NO. 28) |
| Crem | GCTGAGGCTGATGAAAAACA (SEQ ID NO. 29) | GCCACACGATTTTCAAGACA (SEQ ID NO. 30) |
| Sox6 | GACAGCGTTCTGTCATCTCAGCAA (SEQ ID NO. 31) | CGTTCCGGGGTTCCAAAAGTAACA (SEQ ID NO. 32) |
| Tle4 | TTTACAGGCTCAATACCACAGTC (SEQ ID NO. 33) | TGCACAGATAGCATTTAGTCGTT (SEQ ID NO. 34) |
| Bhlhe22 | GGGGAGAGGGAGGTTTAGTG (SEQ ID NO. 35) | CCCTTTCATCACTTGCCAAT (SEQ ID NO. 36) |
| HPRT | CTGGTTAAGCAGTACAGCCCCAAA (SEQ ID NO. 37) | TGGCCTGTATCCAACACTTCGAGA (SEQ ID NO. 38) |
| GAPDH | TGGCAAAGTGGAGATTGTTGCC (SEQ ID NO. 39) | AAGATGGTGATGGGCTTCCCG (SEQ ID NO. 40) |

Cell Culture

HEK-293T and HIT cells (American Type Culture Collection, Manassas, Va.) were maintained in Dullbecco's modified Eagle's medium (DMEM) with 10% fetal bovine serum (FBS), 2 mM L-glutamine, 100 U/ml penicillin, and 100 U/ml streptomycin. Cells were maintained at 37° C. at a 5% $CO_2$ atmosphere in a humidified incubator. HEK-293T cells were transfected with JET-PEI reagent (Poly Plus), while HIT cells were transfected with Lipofectamine™ 2000 Reagent (Invitrogen), both according to the manufacturer's instructions.

Luciferase Activity Assays miR Targeting Assay:

The mouse Bhlhe22 3' UTR (chr3: 17955876-17957373, SEQ ID NO: 41) and Sox6 3' UTR (Chr7:122618117-122619352, SEQ ID NO: 42) were subcloned into psiCHECK-2 Vector (Promega) and transfected into HEK293T cells together with vectors for miRNAs.

Insulin Promoter Regulation:

The overexpression construct: Sox6 [Mouse Annotation: Chromosome 7, NC_000073.5 (122614858 ... 123174561, complement, SEQ ID NO: 73) corresponding to the human Annotation: Chromosome 11, NC_000011.9 (15991795 ... 16497918, complement, SEQ ID NO: 74) MIM: 607257 ID: 55553], Bhlhe22 (pBeta3, amplified and transferred into pacGFP [Mouse Annotation: Chromosome 3, NC_000069.5 (17954402 ... 17957506) ID: 59058, SEQ ID NO: 75, corresponding to the Human Annotation: Chromosome 8, NC_000008.10 (65492814.65496186) MIM: 613483 ID: 27319, SEQ ID NO: 76]. pCDNA3 (Invitrogen) were transfected along with Rat insulin I promoter construct and A20-Renilla luciferase construct.

For both assays, 48 hrs post-transfection, cells were harvested and assayed for Firefly and *Renilla luciferase* activity using Dual luciferase reporter assay system (Promega), according to the manufacturer's instructions.

Histomorphometry

To determine β cell mass, consecutive paraffin sections 5 μm in thickness and 75 μm apart spanning the entire pancreas (approximately 9 sections/pancreas) were stained for insulin and counterstained using Harris' hematoxylin (Sigma). Digital images of sections were obtained at a low magnification (×40) and stitched using NIS-Elements software. The fraction of β cells was determined by measuring the area of insulin immuno-reactivity divided by the area of the whole pancreas, determined by hematoxylin counterstain. The mass of β cells was calculated as the product of pancreas weight and the fraction of tissue covered by β cells.

Statistical Analysis

All statistical analyses were performed using the Student's t-test module of the Microsoft Excel statistical software. Results are displayed as mean±s.e.m of three or more samples/experiments.

Example 1

Disruption of Dicer1 Causes Glucose Intolerance

As Dicer deficiency blocks the output of the entire miRNA repertoire, it provides an opportunity to assess the overall contribution of this network to beta cell function in vivo. Inventors have therefore crossed a Dicer1 conditional allele as previously described by Harfe et al. [Harfe, B. D. et al. (2005) Proc Natl Acad Sci USA 102, 10898-10903] onto an inducible CreER transgene that is driven by the rat insulin promoter (RIP-CreER) previously described by Dor et al. [Dor, Y. et al. (2004) Nature 429, 41-46]. In the resultant RIP-CreER; Dicer1$^{flx/flx}$ mice (called hereafter "βDc$^{null}$", for simplicity), miRNA function is intact until injection of tamoxifen (FIG. 1A). Upon Tamoxifen injection, CreER recombinase inactivates the Dicer1 conditional allele and prevents miRNA processing. Concomitantly, a lacZ/EGFP (Z/EG) reporter transgene [previously described by Novak et al. (2000) Genesis 28, 147-155)], which was crossed into the genetic background of the mouse, is also subject to CreER recombinase activation. Thus, cells in which recombination occurred lose Dicer1 activity and are labeled with EGFP. In control mice, which are heterozygous for the Dicer1 allele RIP-CreER;Dicer1$^{flx/+}$ and also harbor the Z/EG reporter transgene (called hereafter control), tamoxifen induction causes loss of only one Dicer allele and activation of EGFP expression.

A quantitative real-time PCR (qPCR) study of Dicer1 mRNA levels in islets of tamoxifen-treated mice revealed a 50% reduction in Dicer1 expression. Taking into account the relative abundance of beta cells in islets and the incomplete recombination efficiency, it is likely that the level of Dicer1 in the cells that underwent recombination in βDc$^{null}$ animals was close to zero (FIG. 1B). Similarly, representative miRNAs that are characteristic to beta cells (miR7 and miR375) are down regulated in these cells (FIG. 1C).

βDc$^{null}$ animals developed hyperglycemia at two weeks after tamoxifen induction as was evident by blood glucose levels in both fasting (FIG. 2B) and fed animals (FIG. 2A). The hyperglycemia rapidly deteriorated by three weeks post-induction (FIGS. 2A-B). Moreover, βDc$^{null}$ animals were shown to be defective in a glucose tolerance test (GTT), a defect which indicates both phases of insulin secretion are affected (FIGS. 2C-D). Taken together, these results indicate that deletion of Dicer1 in adult beta cells causes overt diabetes.

Example 2

Disruption of Dicer1 Causes a Decrease in Insulin Protein

In order to determine what causes the severe diabetic phenotype, inventors analyzed insulin content of whole pancreata. Compared to controls, βDc$^{null}$ animals showed an 80% decrease in the total insulin content (FIG. 2E), that likely explains the hyperglycemic state. Surprisingly, morphometric analysis of βDc$^{null}$ pancreata, showed that the beta cell mass was not significantly different from that of wild type mice (FIG. 2J). Furthermore, inventors did not detect apoptosis using either TUNEL or activated caspase 3 immunostaining (data not shown).

As the diabetic phenotype of βDc$^{null}$ animals is not caused by loss of beta cells, inventors next evaluated insulin levels in beta cells at the cellular level. Indeed, while immunohistochemical analysis of insulin expression shows a uniform and strong expression in controls (FIGS. 2F-G), in βDc$^{null}$ animals expression of insulin varies from strong in some cells to non-existent in others (FIGS. 2H-I). Examination of GFP expression indicated recombination mosaicisim within the islet, which was due to the incomplete activation of the tamoxifen-induced CreER. This phenomenon was useful in providing an internal wild type control at a single-cell resolution. Thus, inventors could compare insulin levels between cells within the same islet, that is to say, between GFP positive cells (in which recombination occurred) and GFP negative cells (in which recombination had not occurred). When such an analysis was carried out on control pancreata, which are normal for Dicer1 conditional allele but undergo EGFP induction, inventors found that EGFP was co-detected with insulin (FIGS. 3A-D). Notably, in βDc$^{null}$ animals, Dicer-null/EGFP positive cells showed reduced or even total absence of insulin expression (FIGS. 3E-H).

Example 3

Insulin Transcription is Down Regulated in the Dicer1 Null Beta Cells

The observed decrease in insulin expression could result from a defect in any of the steps in insulin production, i.e. transcription, post-transcriptional modification, translation, post-translational processing or degradation. Inventors could not rule out an effect on degradation. However, posttranslational defects were not very likely since the antibody used to detect insulin detected both insulin and pro-insulin. Furthermore, the levels of the insulin processing enzyme Prohormone convertase 1/3 (PC 1/3) were similar between βDc$^{null}$ and control pancreata (FIGS. 7A-F). Thus, the effect of Dicer1 loss was likely earlier—loss of transcriptional or post-transcriptional regulation.

To address a possible effect of miRNA dysregulation on insulin transcription, inventors examined the levels of the two murine insulin transcripts. qPCR performed on isolated islets from mutants showed a 70% decrease in both Insulin1 and Insulin 2 mRNA levels (FIGS. 3I and 3J). Thus, loss of insulin expression originated from changes in insulin mRNA levels.

While regulation of insulin gene expression was primarily at the transcriptional level, posttranscriptional regulation could also play a role, i.e. mRNA levels may be downregulated due to exacerbated mRNA decay. To distinguish between these two possibilities, inventors examined the Cre mRNA levels, a transcript whose expression was driven (artificially) by the insulin promoter, yet its stability was regulated in a separate manner. Inventors found Cre mRNA to be significantly downregulated (FIG. 3K), suggesting that the insulin promoter was transcriptionally less active in βDc$^{null}$ beta cells.

Example 4

Dicer1 Mutant Beta Cells Maintain their Differentiation Markers

Two alternative scenarios may explain loss of insulin transcription. First, if insulin transcription defines the functional identity of mature beta cell, the βDc$^{null}$ beta cells might have lost their identity, regressing into an earlier state of differentiation or even assuming a different cell fate altogether. Alternatively, it may be that a regulatory mechanism that specifically affects insulin transcription is perturbed in the otherwise-intact beta cells.

Analysis of beta cell identity markers revealed that Dicer 1 mutant beta cells (marked by green, FIGS. 4B and 4D) were indistinguishable from their control counterparts (marked by green, FIGS. 4A and 4C). They maintained the expression of the secretory vesicle protein, synaptophysin (marked by red, FIGS. 4A and 4B), and did not express any other hormone marker such as somatostatin, pancreatic polypeptide, glucagon or ghrelin (marked by red, FIGS. 4C and 4D). In order to test whether the cells assumed a progenitor state inventors performed immunostaining for the endocrine progenitor marker, Ngn3, but did not find any expression (data not shown). Therefore, inventors concluded that Dicer1 mutant beta cells maintained endocrine features and did not express alternative fate markers.

In order to further characterize the identity of the Dicer 1 mutant beta cells, inventors analyzed the expression of transcription factors that are typical of mature beta cells, namely Pdx1, MafA, Pax6 and Nkx6.1. Immunostaining of these beta cell markers (marked by red, FIGS. 4E-4L) was similar in GFP positive/Dicer null cells in βDc$^{null}$ mice and GFP positive cells in the control mice (marked by green, FIGS. 4E-4L). Moreover, quantification of these transcriptional activators by qPCR suggested that in the βDc$^{null}$ islets, the expression levels of Pdx1, MafA, Nkx2.2 and Nkx6.1 were comparable with the expression in islets of control littermates (FIG. 5A). Since the nuclear localization of these proteins appeared to be normal (FIGS. 4E-4L), inventors concluded that the repression of the insulin promoter was likely not due to a decrease in the abundance of the transcriptional activators, neither was it related to inadequate compartmentalization. Hence, inventors concluded that βDc$^{null}$ beta cells retained most of their mature molecular identity markers. In fact, the only change inventors observed in the βDc$^{null}$ beta cells was downregulation of insulin expression.

Example 5

Dicer1 Mutant Beta Cells Upregulate the Expression of a Set of Transcriptional Repressors The fact that insulin transcription is downregulated in beta cells that express the chief transcriptional activators of the insulin promoter, could be explained by an abnormal upregulation of transcriptional repressors in βDc$^{null}$ beta cells. Inventors therefore went on to quantify the expression levels of known repressors of insulin synthesis by qPCR. Within the nine repressors that were examined, inventors noted a four-fold increase in the mRNA levels of Sox6 and a three-fold increase in the expression of Bhlhe22. Three other repressors, Crem, Insm1 and Tle4, were upregulated but to a lesser extent, yet in a statistically significant manner (FIG. 5A). Inventors therefore considered Sox6 and Bhlhe22 as prime candidates in controlling the phenotype of βDc$^{null}$ cells downstream of miRNAs, namely the repression of insulin expression.

In order to verify that these repressors can indeed negatively regulate insulin synthesis, inventors next utilized a beta cell culture system. When Sox6 and Bhlhe22 were overexpressed along with a construct harboring luciferase under the control of the rat insulin promoter in cultured HIT cells, inventors were able to recapitulate the reported downregulation of insulin expression. Taken together, these results indicated that the upregulation of Sox6 and Bhlhe22 reduced insulin transcription (FIG. 5B).

Example 6

A Few miRNAs can Regulate Sox6 and Bhlhe22

As Dicer 1 deficiency blocks the output of the entire miRNA repertoire, inventors did not know which miRNAs were responsible for the de-regulation in insulin expression. In order to narrow down the possible miRNAs, inventors took a bioinformatics approach integrating results from the target prediction algorithms TargetScan and Pita as previously described [Bartel, D. P. (2009) Cell 136: 215-233; Kertesz M. et al. (2007) Nat. Genet. 39:1278-84] to identify miRNA binding sites (seed-matches) on the 3'UTR of these mRNAs. Inventors found multiple potential seed matches on the 3'UTR of Sox6 and Bhlhe22 further filtering the list of miRNAs by taking into account only miRNAs which are expressed in pancreatic islets. Inventors identified several miRNA genes that appeared to be expressed in islets and potentially repressed either Sox6 or Bhlhe22 or both (FIG. 6A).

In order to functionally assess potential direct interaction of the candidate miRNAs with Sox6 and Bhlhe22, inventors cloned their 3'UTR into vectors expressing a luciferase reporter. These were transfected separately into HEK293 cells along with vectors for overexpression of various miRNAs. Inventors then analyzed the relative luciferase activity in the presence of different possible targeting miRNAs compared with a non-targeting miRNA. This analysis revealed that, while a few miRNAs had no effect, miR-24, miR-129, miR-15/16, miR-26 and miR-27 interacted with the 3'UTR of Bhlhe22 and repressed the expression of the luciferase reporter by 25-40% (FIG. 6B). Similarly, the 3'UTR of Sox6 was repressed by miR-24, miR182 and miR-375 (FIG. 6C). Interestingly, miR-24 interacted with the 3'UTR of both Sox6 and Bhlhe22 and repressed the expression of the luciferase reporter.

Collectively, our data suggest that miRNAs act to maintain the natural balance between transcriptional repressors and activators of the Insulin 1 and Insulin 2 genes in adult beta cells. Dicer1 deletion causes an imbalance between these transcriptional regulators impacting insulin synthesis. This in turn compromises glucose homeostasis and promotes the rapid onset of diabetes by approximately 40%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08951983B2). An electronic copy of the "Sequence Listing" will also be available from the USPTO upon request and payment of the fee set forth in 37 CFR 1.19(b)(3).

What is claimed is:

1. A method of increasing an insulin content in a pancreatic beta cell, the method comprising expressing in the pancreatic beta cell an exogenous polynucleotide encoding at least one microRNA or a precursor thereof, wherein said microRNA is selected from the group consisting of miR-15, miR-16, miR-24, miR-26, miR-27, miR-129, miR-148, miR-182 and miR-200, thereby increasing the insulin content in the pancreatic beta cell.

2. A method of increasing an insulin content in a pancreatic beta cell in a subject in need thereof, wherein said subject has an insulin deficiency, the method comprising administering to the subject an exogenous polynucleotide encoding at least one microRNA or a precursor thereof, wherein said microRNA is selected from the group consisting of miR-15, miR-16, miR-24, miR-26, miR-27, miR-129, miR-148, miR-182 and miR-200, thereby increasing the insulin content in the pancreatic beta cell in said subject.

3. The method of claim 2, wherein said polynucleotide is operably linked to a cis acting regulatory element active in pancreatic beta cell.

4. The method of claim 2, wherein said insulin deficiency comprises a disease or syndrome selected from the group consisting of type 1 diabetes mellitus, type 2 diabetes mellitus, metabolic syndrome, insulin deficiency syndrome, maturity onset diabetes of the young (MODY 1-11) and permanent neonatal diabetes mellitus.

5. The method of claim 2, wherein said subject is a human subject.

* * * * *